United States Patent
Masere

(10) Patent No.: US 11,396,629 B2
(45) Date of Patent: Jul. 26, 2022

(54) QUINONE METHIDE AND AMMONIUM SALT ANTIPOLYMERANT COMPOSITION AND METHOD

(71) Applicant: Ecolab USA Inc., St. Paul, MN (US)

(72) Inventor: Jonathan Masere, Richmond, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 17/067,164

(22) Filed: Oct. 9, 2020

(65) Prior Publication Data
US 2021/0108141 A1  Apr. 15, 2021

Related U.S. Application Data

(60) Provisional application No. 62/913,934, filed on Oct. 11, 2019.

(51) Int. Cl.
| | | |
|---|---|---|
| C09K 15/08 | (2006.01) | |
| C09K 15/18 | (2006.01) | |
| C07C 7/20 | (2006.01) | |

(52) U.S. Cl.
CPC ............ *C09K 15/08* (2013.01); *C07C 7/20* (2013.01); *C09K 15/18* (2013.01)

(58) Field of Classification Search
CPC ........ C09K 15/08; C09K 15/15; C09K 15/16; C07C 7/20; C07B 63/04; C08F 2/00; C08F 2/38; C08F 2/40; C08F 2/42
USPC ............... 252/401, 403, 404, 405; 203/8, 9; 585/2, 3, 4, 5
See application file for complete search history.

(56) References Cited

U.S. PATENT DOCUMENTS

| | | | |
|---|---|---|---|
| 2,595,225 A | | 5/1952 | Coffman |
| 3,230,225 A | * | 1/1966 | Arrigo .................... C07C 15/46 585/2 |
| 3,674,651 A | | 7/1972 | Otsuki et al. |
| 4,003,800 A | | 1/1977 | Bacha et al. |
| 4,247,476 A | | 1/1981 | Haase et al. |
| 4,539,383 A | | 9/1985 | Taylor |
| 4,929,778 A | * | 5/1990 | Roling ...................... C07C 7/20 252/403 |
| 5,500,330 A | | 3/1996 | Szajewski et al. |
| 5,583,247 A | * | 12/1996 | Nesvadba ................. C07C 7/20 560/2 |
| 5,616,774 A | * | 4/1997 | Evans ...................... C07C 7/20 252/182.18 |

(Continued)

FOREIGN PATENT DOCUMENTS

| | | |
|---|---|---|
| WO | 2016172076 A1 | 10/2016 |

OTHER PUBLICATIONS

Motyakin, et al. (2004) "Inhibitor Radicals in Styrene Polymerization", Journal of Applied Polymer Science, 91:1599-1603.

(Continued)

*Primary Examiner* — Matthew R Diaz
(74) *Attorney, Agent, or Firm* — Kagan Binder, PLLC

(57) ABSTRACT

Described are compositions and methods for inhibiting polymerization of a monomer (e.g., styrene) composition a quinone methide polymerization retarder and an ammonium salt. In a mixture, the ammonium salt improves the efficacy of the quinone methide polymerization retarder and provides greater antipolymerant activity. In turn, the mixture reduces or prevents apparatus fouling and improves the purity of monomer streams.

25 Claims, 3 Drawing Sheets

(56) References Cited

U.S. PATENT DOCUMENTS

| | | | |
|---|---|---|---|
| 5,648,573 A | 7/1997 | Arhancet et al. | |
| 6,024,894 A * | 2/2000 | Arhancet | C09K 15/14 |
| | | | 252/404 |
| 6,200,461 B1 * | 3/2001 | Eldin | C09K 15/18 |
| | | | 208/48 AA |
| 6,770,222 B1 * | 8/2004 | Ukita | C09K 15/20 |
| | | | 252/399 |
| 7,045,647 B2 * | 5/2006 | Benage | C09K 15/08 |
| | | | 585/4 |
| 7,651,635 B1 * | 1/2010 | Lewis | C07C 7/20 |
| | | | 252/404 |
| 7,723,398 B2 * | 5/2010 | Ilg | C07B 63/04 |
| | | | 522/78 |
| 8,383,753 B2 | 2/2013 | Klosin et al. | |
| 8,766,027 B1 * | 7/2014 | Subramaniyam | C09K 15/24 |
| | | | 585/428 |
| 9,090,526 B2 | 7/2015 | Masere | |
| 9,133,288 B2 | 9/2015 | Loyns et al. | |
| 9,234,057 B2 | 1/2016 | Subramaniyam | |
| 9,266,797 B2 | 2/2016 | Colorado, Jr. et al. | |
| 9,598,333 B2 | 3/2017 | Subramaniyan | |
| 9,957,209 B2 * | 5/2018 | Masere | C07C 7/20 |
| 2005/0113625 A1 * | 5/2005 | Benage | C09K 15/04 |
| | | | 208/48 AA |
| 2006/0062753 A1 | 3/2006 | Naraghi et al. | |
| 2006/0163539 A1 * | 7/2006 | Nakajima | C07C 7/20 |
| | | | 252/397 |
| 2007/0208204 A1 * | 9/2007 | Meyer | C07C 7/20 |
| | | | 585/4 |
| 2010/0311849 A1 | 12/2010 | Gonzalez Montiel et al. | |
| 2011/0230588 A1 | 9/2011 | Devlin et al. | |
| 2020/0017610 A1 | 1/2020 | Masere et al. | |

OTHER PUBLICATIONS

Yachigo, et al. (1992) "Studies on polymer stabilizers: Part IV—Prevention of oxidative discoloration", Polymer Degradation and Stability, 37:107-113.

Eike, et al. (2003) "Predicting melting points of quaternary ammonium ionic liquids", Green Chemistry, 5:323-328.

* cited by examiner

QUINONE METHIDE AND AMMONIUM SALT ANTIPOLYMERANT COMPOSITION AND METHOD

CROSS REFERENCE TO RELATED APPLICATION

This application claims the benefit of U.S. Provisional Patent Application Ser. No. 62/913,934, filed Oct. 11, 2019, the disclosure of which is incorporated by reference herein in its entirety.

TECHNICAL FIELD

The invention is directed to compositions that include a quinone methide and an amine salt and use of this combination as an antipolymerant composition to prevent premature polymerization of monomers.

BACKGROUND

The high-temperature processing of hydrocarbon stream laden with ethylenically unsaturated monomers like styrene, isoprene, butadiene, for instance can be very challenging. In various chemical industrial processes, the use of high temperatures to purify said monomers can lead to unwanted and problematic polymers. These vinylic monomers undesirably polymerize through radical polymerization especially at elevated temperatures. Similarly, transportation and storage of hydrocarbon streams containing vinylic species can lead to premature polymerization unless antipolymerants are added to said streams. The polymer thus formed can precipitate from solution to foul the process equipment. These undesirable polymerization reactions also result in a loss in the production efficiency and the consumption of valuable products. Removing the foulants becomes necessary. The physical removal or cleaning of the fouled equipment is often expensive. Undesired polymerization reactions are particularly problematic in compositions having vinyl aromatic monomers To prevent undesired polymerization reactions, free-radical polymerization antipolymerants are often added to process streams or stored compositions. However, these compounds are generally consumed quite rapidly. For example, in cases of emergency due to a mechanical or processing problems and where more inhibitor cannot be added, previously added inhibitor will be rapidly consumed. Subsequently, unwanted polymerization reactions will then rapidly recur.

Examples of polymerization inhibitors known in the art include dialkylhydroxylamines, such as hydroxypropylhydroxylamine (HPHA), and stable nitroxide free radicals. Other inhibitors include N,N'-dialkylphenylenediamines, N,N'-diarylphenylenediamines and N-aryl-N'-alkylphenylene-diamines. Quinone diimide compounds are also another class of inhibitors.

Antipolymerants such as sulfur and dinitrophenol (DNP) compounds exemplified by 2,6-dinitrophenol, 2,4-dinitrocresol, and 2-sec-butyl-4,6-dinitrophenol (DNBP), were initially used. However DNP and sulfur antipolymerants release $NO_x$ and $SO_x$ emissions, making their use problematic. Furthermore, DNP-based antipolymerants are highly toxic such that the safety of personnel handling DNP-based antipolymerants is a major concern.

Other types of antipolymerant compounds often referred to as "retarders" slow down the rate of polymerization reactions. However, they are not as effective as polymerization inhibitors, particularly stable nitroxide free radicals. Polymerization retarders, however, are usually not consumed as quickly as polymerization inhibitors so they tend to be more useful in cases of emergency shutdowns.

One class of compounds designed to function as a safer substitute for DNP retarders is based on quinone methide chemistry. Quinone methides slow the rate of polymer formation under static conditions and do not need to be frequently re-fed into the process stream. Some quinone methide compounds, however, do not exhibit good stability, or may not be as effective in inhibiting rate of polymerization as compared to DNP- and other NO-based antipolymerants. Examples of quinone methide compounds are in U.S. Pat. Nos. 4,003,800, 5,583,247, and 7,045,647.

Technical challenges remain in this area of technology relating to the efficacy of compounds used to inhibit or slow polymerization reactions, as well as stability and safety concerns. In spite of the concerns over toxicity, DNP-based antipolymerants remain the most efficient retarders available. Out of safety concerns, there is a need for antipolymerant formulations that are at least as efficacious as DNP-type retarders, but non-toxic.

SUMMARY

The current disclosure is directed to compositions and methods that include or utilize a polymerization retarder that is a quinone methide, and an ammonium salt. The ammonium salt improves the antipolymerant efficacy of the quinone methide, in various embodiments to levels comparable to nitro group- or nitroxide group-containing antipolymerants. The composition and method can be used to inhibit the polymerization of ethylenically unsaturated monomers like styrene and butadiene in various processes and situations, such as purification, fractionation, separation, compression, transportation, and storage of various compositions. The use of the inventive compositions also mitigates the fouling of process, transportation and storage equipment. In turn, polymer contamination of purified monomer products can be drastically reduced, and maintenance costs of equipment used to produce such monomer products is also reduced.

In embodiments, the invention provides a composition comprising a quinone methide and ammonium salt.

Exemplary quinone methides are compounds of Formula I:

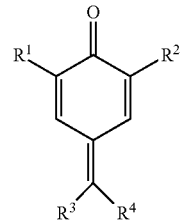

wherein $R^1$ and $R^2$ are independently selected from C4-C18 alkyl, C5-C12 cycloalkyl, phenyl, and C7-C15 cycloalkyl, wherein $R^3$ and $R^4$ are independently selected from —H, C1-C18 alkyl, phenyl, substituted phenyl, C5-C12 cycloalkyl, —CN, —COOH, —C=$CHR^5$, —C≡$CR^5$, —$COOR^5$, —$COR^5$, —$OCOR^5$, —$CONHR^5$, wherein $R^5$ is selected from H, C1-C18 alkyl, C5-C12 cycloalkyl, phenyl, and C7-C15 cycloalkyl, and substituted phenyl.

In some embodiments, the quinone methide retarder is a compound of the Formula II:

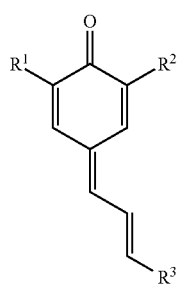

wherein R¹ and R² are independently selected from hydrogen, C4-C18 alkyl, C5-C12 cycloalkyl, aryl, C7-C15 arylalkyl, and C7-C15 alkylaryl; and wherein R³ is selected from hydrogen, C1-C18 alkyl, C5-C12 cycloalkyl, C5-C12 heterocycloalkyl, aryl, C7-C15 arylalkyl, and C7-C15 alkylaryl.

In some embodiments, R¹ and R² are independently selected from hydrogen, C4-C18 alkyl, or more specifically independently selected from t-butyl, t-amyl, t-hexyl, t-octyl, or t-decyl. In some embodiments, R³ is selected from aryl, C7-C15 arylalkyl, and C7-C15 alkylaryl, and more specifically is aryl.

Exemplary ammonium salts include cations of Formula III:

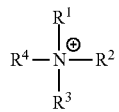

where R¹, R², R³, and R⁴ are independently selected from (a) —H, (b) a carbon-containing group, (c) an oxygen-containing group, (d) an oxygen- and carbon-containing group. Exemplary cations include monoprotonated ammonium cations, diprotonated ammonium cations, triprotonated ammonium cations, and quaternary ammonium cations.

A quaternary ammonium cation refers to one wherein the nitrogen is directly bonded to a carbon atom in each of R¹, R², R³, and R⁴. For example, a quaternary ammonium cation can be one where R², R³, and R⁴ are independently selected from alkyl, aryl, arylalkyl, and alkylaryl.

Other exemplary ammonium salts include cations of Formula IV:

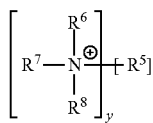

where R⁵ is a monovalent or multivalent carbon-containing group, y is an integer in the range of 1-4, and R⁶, R⁷, and R⁸ are independently selected from (a)-(d) as described with reference to Formula I.

Exemplary ammonium salts include an anion that includes a carboxylate group, such as acetate, propionate, butyrate, isobutyrate, valerate, isovalerate, 2-methylbutanoate, pivalate, caproate, 2-methylvalerate, 3-methylvalerate, 4-methylvalerate, 2,2-2,2-dimethylbutanoate, 2-ethylbutanoate, heptanoate, 2-methylcaproate, 3-methylcaproate, 4-methylcaproate, 5-methylcaproate, 2,2-dimethylvalerate, 2-ethylvalerate, caprylate, 2-methylheptanoate, 3-methylheptanoate, 4-methyl heptanoate, 5-methylheptanoate, 6-methylheptanoate, 2,2-dimethylcaproate, 2-ethylcaproate, and 2-propylvalerate, and combinations thereof.

In embodiments, the ammonium salt has the properties of an ionic liquid at room temperature.

In embodiments, the quinone methide is present in a molar amount greater than the ammonium salt.

In embodiments, the composition of the disclosure is used for inhibiting monomer polymerization in a composition. In embodiments, the composition of the disclosure is used for a polymerizable monomer synthesis, refining, or purification process. In embodiments, the composition of the disclosure is used for polymerizable monomer storage or transport.

In embodiments, the invention provides a method for inhibiting the polymerization of monomers in a composition. The method includes providing a composition comprising polymerizable monomer or a compound capable of forming a polymerizable monomer, a quinone methide, and an ammonium salt. The composition can be provided by adding the quinone methide and the ammonium salt to the composition at the same time or at different times. In the composition, the polymerization of polymerizable monomer is inhibited in the presence of the quinone methide and the ammonium salt.

With reference to the combinations of exemplary quinone methides (QMCinn, QMPh) and exemplary ammonium salts (TIPA-2-EH, DIHA-2-EH) and experimental studies described herein, the combinations provided improved antipolymerant activity over composition having the quinone methide alone, and even improved antipolymerant activity over the nitro-group containing antipolymerant DNBP. The improvement was seen throughout the course of the antipolymerant test period.

In embodiments, the polymerizable monomer comprises a vinyl or ethylenically unsaturated group, or is selected from the group consisting of acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyltoluene, and vinylpyridine.

In embodiments, the method is performed during purification or processing of one or more components of the composition, and/or is performed prior to storage or transport of the second composition.

DETAILED DESCRIPTION

Figure 1:
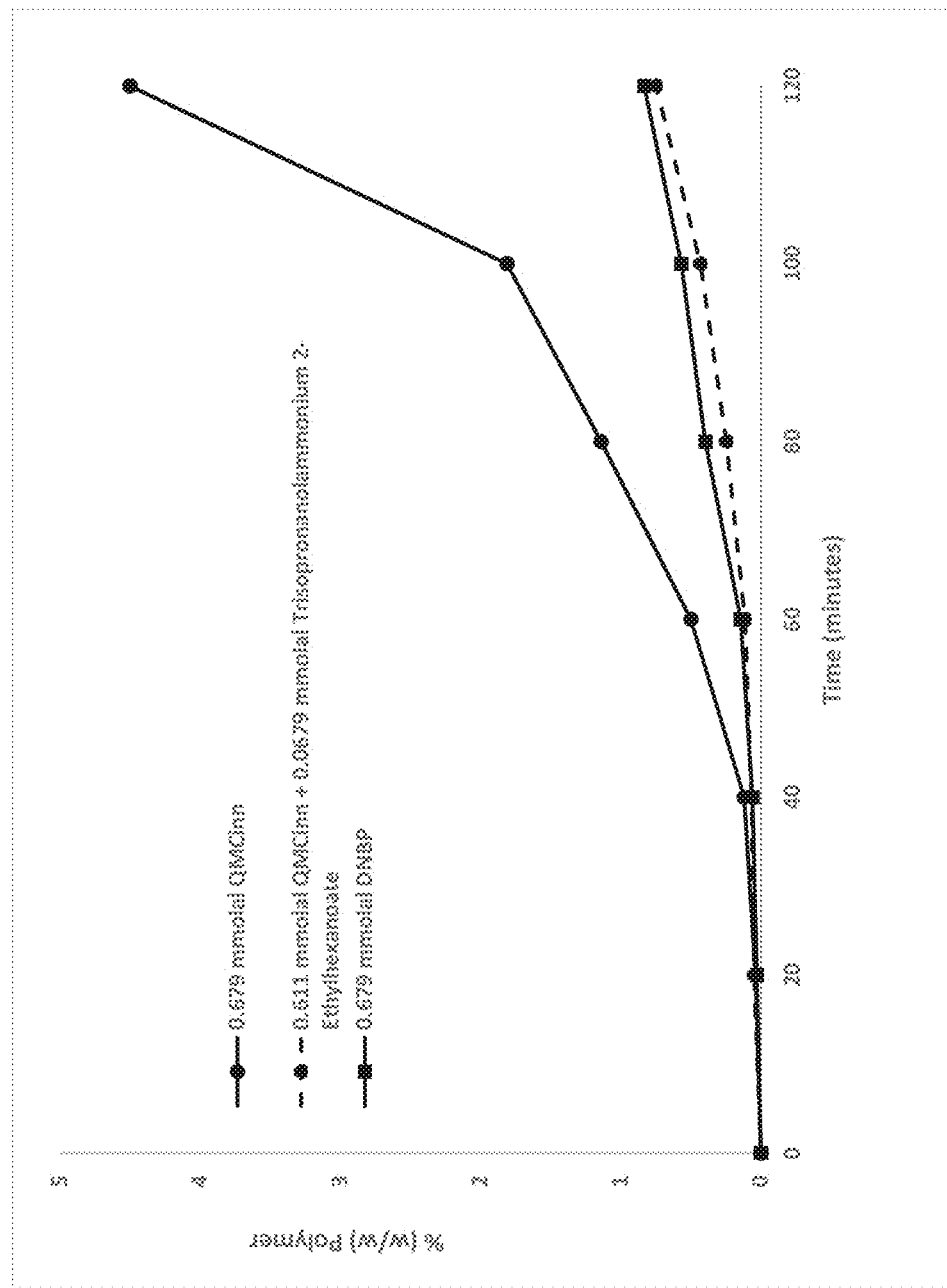
FIG. 1 is a graph of the amount of polystyrene polymer formed from a styrene monomer solution in the presence of a quinone methide polymerization retarder (7-Cinnamyl Quinone Methide; QMCinn) in combination with an ammonium salt (triisopropanolammonium 2-ethylhexanoate; TIPA-2-EH), and compared to QMCinn and nitrophenol-based polymerization inhibitor (DNBP), used alone.
Figure 2:
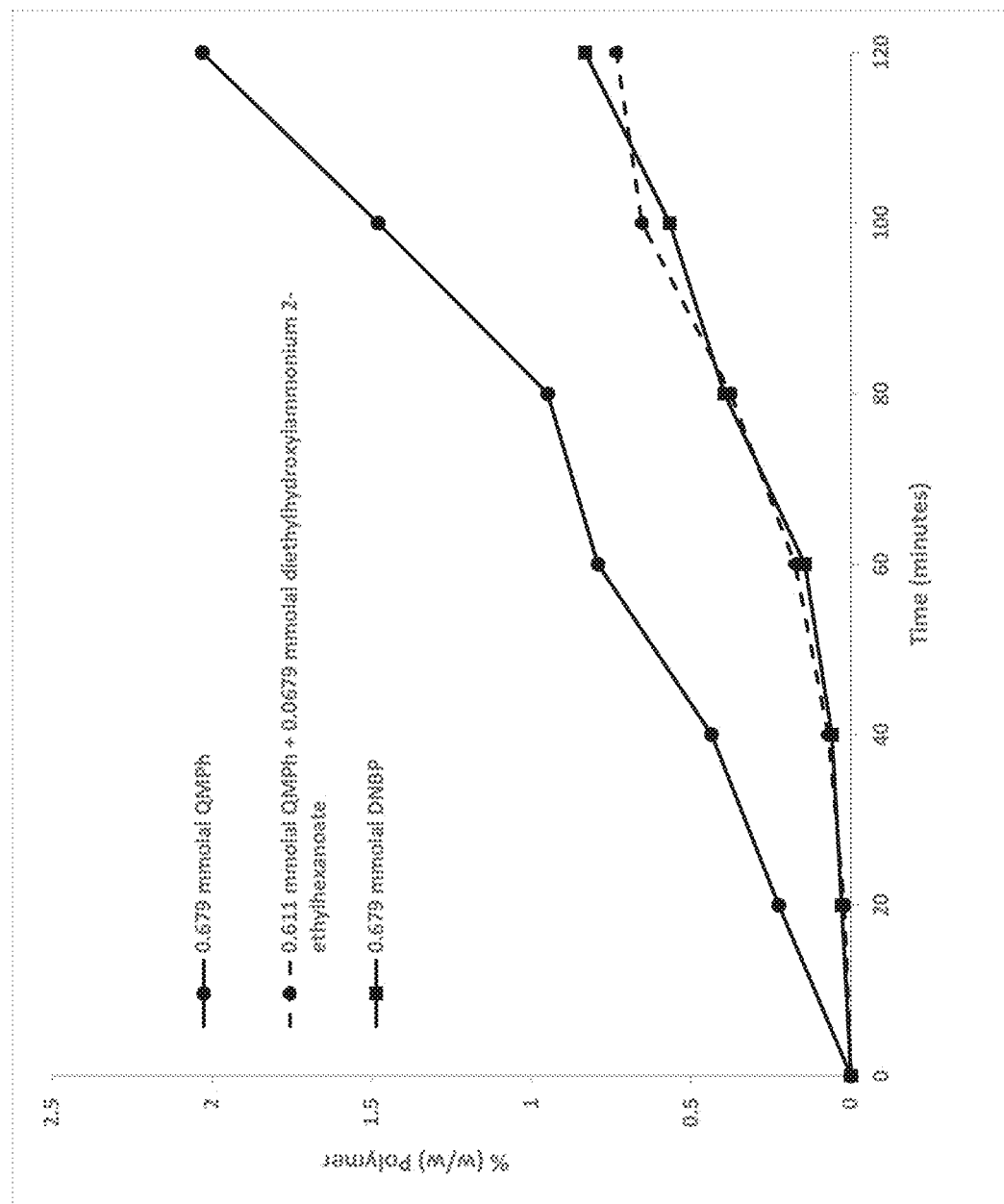
FIG. 2 is a graph of the amount of polystyrene polymer formed from a styrene monomer solution in the presence of quinone methide polymerization retarder (7-Phenyl Quinone Methide; QMPh), in combination with a different ammonium salt (diethylhydroxylammonium 2-ethylhexanoate; DEHA-2-EH), and compared to QMPh and DNBP, used alone.
Figure 3:
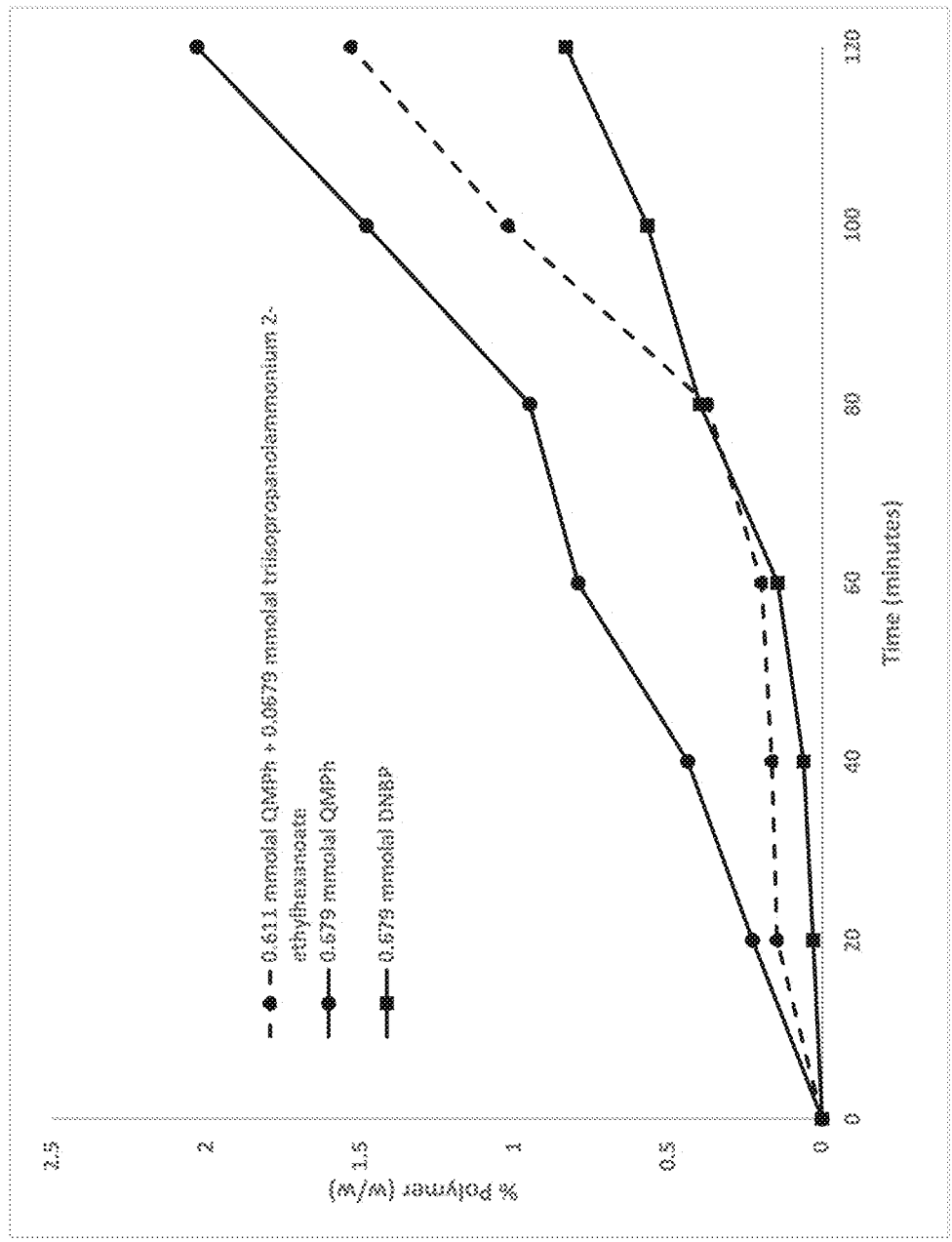
FIG. 3 is a graph of the amount of polystyrene polymer formed from a styrene monomer solution in the presence of a quinone methide polymerization retarder QMPh and TIPA 2-EH, and compared to QMPh and nitrophenol-based polymerization inhibitor (DNBP), used alone.

Although the present disclosure provides references to preferred embodiments, persons skilled in the art will recognize that changes may be made in form and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

Additional advantages and novel features of the invention will be set forth in part in the description that follows, and in part will become apparent to those skilled in the art upon examination of the following, or may be learned through routine experimentation upon practice of the invention.

The disclosure provides compositions that include a quinone methide polymerization retarder and an ammonium salt for use in compositions to prevent unwanted formation of polymer. The ammonium salts can improve the antipolymerant efficacy of the quinone methide polymerization retarder and in turn provide better antipolymerant activity when used in a monomer-containing composition. The disclosure also provides methods which use the quinone methide polymerization retarder and ammonium salt in a method for inhibiting the polymerization of monomers in a monomer-containing composition, such as a vinyl aromatic monomer-containing composition.

Aspects of the disclosure provide a composition for inhibiting monomer polymerization that includes a quinone methide polymerization retarder and an ammonium salt. Optionally the composition can include one or more other components, such as an organic solvent. Other antipolymerants, such as a nitroxide-group containing polymerization inhibitor, can optionally be used or can be excluded from compositions of the disclosure.

A composition that includes these components (and any one or more optional component) can be in a desired form, such as in a liquid form, a dry form, or as a suspension or dispersion. The quinone methide and ammonium salt can be in desired physical states in the composition, such as in a dissolved state, in a partially dissolved state, in a suspended state, or in a dry mixture. Also, the quinone methide and ammonium salt can be in desired forms in the composition, such as optionally in particulate forms. If one or more of the components is in a particulate form, the particles can optionally be described in terms of particle size (e.g., particles of a size range) and/or shape. The form of the composition and the state of the components therein can be chosen by selection of quinone methide and ammonium salt, with an understanding of the physical property of each compound. The form of the composition and the state of the components therein can also be affected by the inclusion of one or more optional components, such as a solvent, or solvent mixture, or other excipient compounds like surfactants, dispersants, etc. The form of the composition and the state of the components therein can also be affected by temperature, and composition properties may optionally be described in circumstances at a particular temperature (e.g., at a storage temperature such as 5° C. or below, at room temperature (25° C.), or at a temperature used for monomer synthesis and/or processing (e.g., about 100° C. or greater, about 150° C., about 175° C., etc.).

In preferred embodiments, the ammonium salt is in liquid form (e.g., such as in the form of an "ionic liquid"). An ammonium salt that is in liquid form can be determined in a certain temperature range. The ammonium salt may be described as being a liquid at a certain temperature, such as about room temperature (~25° C.). Physical properties of the ammonium salt are typically determined when it is in pure or substantially pure form.

In embodiments, the ammonium salt can be in liquid form at both storage and working temperatures. A "storage temperature" can be one in the range of about 5° C. to about 40° C., or about 15° C. to about 30° C. A typical storage temperature is room temperature. A "working temperature" can be one or more temperatures commonly used for refining or processing monomer streams, such as a temperature greater than 50° C., greater than 80° C., such as in the range of about 100° C. to about 400° C., about 100° C. to about 200° C., or about 100° C. to about 150° C.

In embodiments, the ammonium salt can be in a solid form at a storage temperature, and a liquid at a working temperature. For example, the ammonium salt can in solid form at a temperature below about 50° C., below about 40° C., below about 30° C., below about 20° C., or below about 10° C., and can be a liquid at a temperature greater than about 50° C., greater than about 80° C., or greater than about 100° C. For example, in some embodiments the ammonium salt can have a melting point in the range of about 10° C. to about 100° C., or about 10° C. to about 80° C.

Eike, D. M., et al. (Green Chemistry, 5:323-328, 2003) describes a Quantitative Structure-Property Relationship (QSPR) method to correlate and predict the melting points of organic salts based on the ammonium cations.

As discussed herein, the composition including the quinone methide and ammonium salt can optionally include other components in the composition (e.g., described in terms of a composition "comprising" the quinone methide and ammonium salt). For example, such compositions can include other components such as a solvent, surfactants, dispersants, etc. If an optional component is present in the composition it may be described in terms of a weight amount relative to one or both of the quinone methide and ammonium salt in the composition. The optional component may be present in a weight amount greater than, or an amount less than, either the quinone methide or the ammonium salt, or the total amount of quinone methide and ammonium salt.

A composition that includes the quinone methide and ammonium salt, and any one or more optional component (s), can be described in terms of the amount of components, by weight, in relationship one another. In a composition wherein a certain component is the "predominant" component, that component is greater than any other component by weight. For example, in a composition wherein components A, B, and C are present at 48% (wt), 47% (wt), and 5% (wt), component A is the predominant component in the composition. If component A is in an amount greater than 50% (wt) of the composition it constitutes the majority of the composition.

As used herein, the term "optional" or "optionally" means that the subsequently described object (e.g., compound), event (e.g., processing step), or circumstance may, but need not occur, and that the description includes instances where the object, event, or circumstance occurs and instances in which it does not.

Compositions of the disclosure can include those recited compounds and optionally can include other components in the composition but in very small amounts (e.g., described in terms of a composition "consisting essentially of" the recited components). For example, such compositions can include one or more other components but not in an amount that is greater than about 1% (wt), about 0.5% (wt), or about 1% (wt), of the total composition. A composition that consists essentially of the quinone methide and ammonium salt (for example, dissolved in a solvent) can optionally include one or more other components but in an amount less than about 1% (wt) of the total composition. In a composition "consisting of" the recited components there is no other measurable amount of component other than the recited component.

As used herein, the terms "substantially" and "consisting essentially of" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of nonlimiting examples thereof, dispersibility, stability, rate, solubility, and the like; intended values include weight of a component added, concentration of components added, and the like. The effect on methods that are modified include the effects caused by variations in type or amount of materials used in a process, variability in machine settings, the effects of ambient conditions on a process, and the like wherein the manner or degree of the effect does not negate one or more intended properties or results; and like proximate considerations. Where modified by the term "substantially" or "consisting essentially of", the claims appended hereto include equivalents to these types and amounts of materials.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe any range of values, for example "about 1 to 5" the recitation means "1 to 5" and "about 1 to about 5" and "1 to about 5" and "about 1 to 5" unless specifically limited by context.

Compositions and methods of the disclosure include or use a polymerization retarder that has a quinone methide chemistry. Quinone methides are chemically characterized by a cyclohexadiene group (or derivative thereof), a carbonyl group, and an exocyclic methylene group. Monocyclic quinone methides are well known as polymerization retarders, but polycyclic (bicyclic, tricyclic, etc.) quinone methide compounds are also known.

In some embodiments, the quinone methide retarder is a compound of the Formula I:

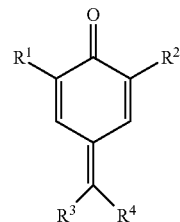

wherein $R^1$ and $R^2$ are independently selected from C4-C18 alkyl, C5-C12 cycloalkyl, phenyl, and C7-C15 cycloalkyl, wherein $R^3$ and $R^4$ are independently selected from —H, C1-C18 alkyl, phenyl, substituted phenyl, C5-C12 cycloalkyl, —CN, —COOH, —C=CHR$^5$, —C≡CR$^5$, —COOR$^5$, —COR$^5$, —OCOR$^5$, —CONHR$^5$, wherein $R^5$ is selected from H, C1-C18 alkyl, C5-C12 cycloalkyl, phenyl, and C7-C15 cycloalkyl, and substituted phenyl. In preferred embodiments, $R^1$ and $R^2$ are independently selected from C4-C18 alkyl, and preferably C4-C6 linear or brached alkyl, such as tert-butyl.

Exemplary the quinone methide retarders include, 2,6-di-tert-butyl-4-benzylidene-cyclohexa-2,5-dienone, 2,6-di-tert-butyl-4-(4-nitrobenzylidene)-cyclohexa-2,5-dienone, 2,6-di-tert-butyl-3-(4-nitrobenzylidene)-cyclohexa-2,5-dienone, 2,6-di-tert-butyl-4-(4-cyanobenzylidene)-cyclohexa-2,5-dienone, 2,6-di-tert-butyl-4-(4-methoxybenzylidene)-cyclohexa-2,5-dienone and 2,6-di-tert-butyl-4-(3,5-di-tert-butyl-4-hydroxybenzylidene)-cyclohexa-2,5-dienone. See, for example, U.S. Pat. No. 5,616,774 and U.S. App. Pub. No. 2006/0163539.

The exemplary quinone methide 2,6-di-tert-butyl-4-benzylidene-cyclohexa-2,5-dienone has the following structure:

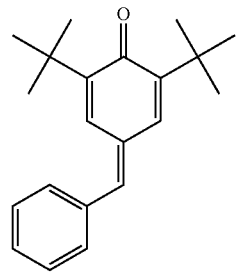 [SMILES: CC(C)(C)C1=CC(=Cc2ccccc2)C=C(C(C)(C)C)C1=O]

and is referred to as "7-Phenyl Quinone Methide" and "QMPh" or "PhQM" herein.

In some embodiments, the quinone methide retarder is a compound of the Formula II:

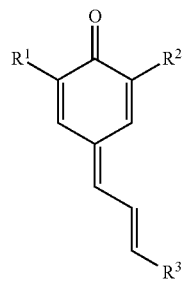

wherein $R^1$ and $R^2$ are independently selected from hydrogen, C4-C18 alkyl, C5-C12 cycloalkyl, aryl, C7-C15 arylalkyl, and C7-C15 alkylaryl; and wherein $R^3$ is selected from hydrogen, C1-C18 alkyl, C5-C12 cycloalkyl, C5-C12 heterocycloalkyl, aryl, C7-C15 arylalkyl, and C7-C15 alkylaryl.

In some embodiments, $R^1$ and $R^2$ are independently selected from hydrogen, C4-C18 alkyl, or more specifically independently selected from t-butyl, t-amyl, t-hexyl, t-octyl, or t-decyl. In some embodiments, $R^3$ is selected from aryl, C7-C15 arylalkyl, and C7-C15 alkylaryl, and more specifically is aryl.

Exemplary quinone methides of Formula II include 2,6-di-tert-butyl-4-(3-phenylallylidene)cyclohexa-2,5-dienone (herein referred to as "7-Cinnamyl Quinone Methide" and "7-Cinn-QM") and are described in U.S. Pat. No. 9,957,209 (Masere and Colorado), the disclosure of which is incorporated herein by reference. 7-Cinn-QM has the following structure:

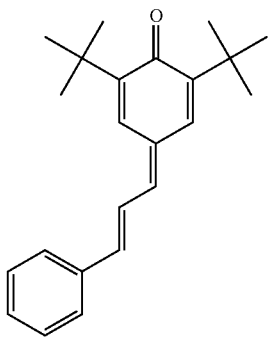 [SMILES: CC(C)(C)C1=CC(=C/C=C/c2ccccc2)C=C(C(C)(C)C)C1=O]

The ammonium salt of the disclosure can provide an improvement with regards to the efficacy of the quinone methide polymerization retarder when used in combination (as compared to a composition that does not include the ammonium salt). Without being bound by a particular theory or mechanism, the ammonium salt may enhance the functionality of the quinone methide retarder. For example, the ammonium salt may enhance the ability of the quinone methide retarder to retard polymerization, or may enhance the functional life of the quinone methide retarder, thereby allowing it to retard polymerization more effectively over a period of time.

Compositions and methods of the disclosure include or use of an ammonium salt. The ammonium salt includes an ammonium-containing cation and an anion. The ammonium-containing cation can be symmetric, such as in cases where four R groups bonded to the positively-charged nitrogen are identical, or asymmetric, such as in cases where there are one or more differences among the four R groups bonded to the positively-charged nitrogen. In many embodiments, the ammonium-containing cation is protonated, wherein one or more of the four R groups bonded to the nitrogen of the ammonium salt is or are hydrogen. Exemplary ammonium cations include monoprotonated ammonium cations, diprotonated ammonium cations, and triprotonated ammonium cations.

The anion of the ammonium salt can be an organic anion or an inorganic anion. In some embodiments, the anion is derived from an acidic compound, such as one derived from a carboxylic acid, a sulfonic acid, a nitric acid, a phosphonic acid, or a combination thereof. Accordingly, exemplary anions include carboxylate, sulfonate, nitrate, phosphate, etc.

In embodiments, the ammonium salt comprises a cation of the Formula III:

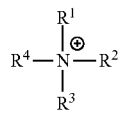

In Formula III, $R^1$, $R^2$, $R^3$, and $R^1$ are independently selected from (a) —H, (b) a carbon-containing group, (c) an oxygen-containing group, (d) an oxygen- and carbon-containing group.

Other exemplary ammonium salts include a cation of Formula IV:

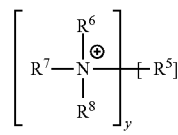

where $R^5$ is a monovalent or multivalent carbon-containing group, y is an integer in the range of 1-4, and $R^6$, $R^7$, and $R^8$ are independently selected from (a)-(d) as described.

In certain embodiments of Formula III, at least three of $R^1$, $R^2$, $R^3$, and $R^4$ are any one or a combination of (b)-(d). In certain embodiments of Formula IV, at least two of $R^6$, $R^7$, and $R^8$ are any one or a combination of (b)-(d). In embodiments of Formula III or IV, (b) the carbon-containing group can consist of carbon, oxygen, and hydrogen, (c) the oxygen-containing group can consist of oxygen and hydrogen, (d) the oxygen- and carbon-containing group can consist of carbon, oxygen, and hydrogen, or any combination of (b)-(d). In those compounds of Formulas III and IV that consist of certain atoms, no other atom types other than those described are present in the groups. In embodiments having groups that consist of certain atoms, the cation of the ammonium salt can have (a) a total amount of carbon atoms in the range of 0-18, 1-12, or 2-10; (b) a total amount of oxygen atoms in the range of 0-6, 1-4, or 1-3; (c) a total amount of hydrogen atoms in the range of 4-40, 6-30, or 8-24; or any combination of (a)-(c).

In other embodiments, R groups of Formulas III and IV can include the recited atoms or chemistries, and optionally include other atoms or chemistries. Exemplary groups that include oxygen atom(s) can include chemistries such as hydroxyl, carbonyl, ester, and ether. In embodiments, one or more of $R^1$, $R^2$, $R^3$, and $R^4$ of Formula III, or $R^6$, $R^7$, and $R^8$ of Formula IV has one oxygen-containing group selected from hydroxyl, carbonyl, ester, and ether. In embodiments, one or more of $R^1$, $R^2$, $R^3$, and $R^4$ of Formula III has two or three oxygen-containing groups, or $R^6$, $R^7$, and $R^8$ of Formula IV has one or two oxygen-containing groups, the oxygen-containing groups selected from hydroxyl, carbonyl, ester, and ether, or a combination thereof.

In some embodiments, in the ammonium salt, one, two, three, or four of $R^1$, $R^2$, $R^3$, and $R^4$ of Formula III, or one, two, three of $R^6$, $R^7$, and $R^8$ of Formula IV are independently selected from oxygen- and carbon-containing group(s) that are linear or branched C1-C18 hydroxyalkyl or C6-C18 hydroxyaryl groups, linear or branched C1-C12 hydroxyalkyl or C6-C12 hydroxyaryl groups, linear or branched C1-C8 hydroxyalkyl groups or C6-C8 hydroxyaryl groups, or linear or branched C1-C6 hydroxyalkyl groups or a C6 hydroxyaryl group. Exemplary hydroxyalkyl groups include hydroxymethyl, 1- or 2-hydroxyethyl, 1-, 2-, or 3-hydroxypropyl, 2-hydroxyisopropyl, 1-, 2-, 3-, or 4-hydroxybutyl, and 1-, 2-, or 3-hydroxyisobutyl. An exemplary hydroxyaryl group is 2-hydroxyphenyl.

In some embodiments in the ammonium salt, one, two, three, or four of $R^1$, $R^2$, $R^3$, and $R^4$ of Formula III, or one, two, three of $R^6$, $R^7$, and $R^1$ of Formula IV have an oxygen- and carbon-containing group of the Formula VIII:

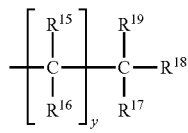

where $R^{15}$, $R^{16}$, $R^{17}$, $R^{18}$, and $R^{19}$ are independently selected from H, $C_1$-$C_{18}$ alkyl, aryl, alkyl aryl, aryl alkyl, and —$OR^{20}$, wherein $OR^{20}$ has the same meaning as any of $R^{15}$-$R^{19}$, wherein Formula VIII includes at least one —$OR^{20}$ group, and in some embodiments one —$OR^{20}$ group, or $R^{16}$ and $R^{17}$ are divalent hydrocarbon-containing groups bonded to one another to form a cyclic alkyl or aryl group, and wherein y is an integer in the range of 1-3.

In some embodiments in the ammonium salt, one, two, three, or four of $R^1$, $R^2$, $R^3$, and $R^4$ of Formula III, or one, two, three of $R^6$, $R^7$, and $R^1$ of Formula IV have an oxygen- and carbon-containing group of the Formula V:

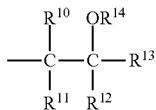

where $R^{10}$, $R^{11}$, $R^{12}$, $R^{13}$ and $R^{14}$ are independently selected from H, $C_1$-$C_{18}$ alkyl, aryl, alkyl aryl, and aryl alkyl.

Some exemplary cations of Formula VIII include those wherein $R^{16}$ and $R^{17}$ are divalent hydrocarbon-containing groups bonded to one another to form a cyclic alkyl or aryl group, such as N,N,N-tris(2-hydroxyphenyl)ammonium, and N,N-bis(2-hydroxyphenyl)hydroxylammonium.

In some embodiments, in the ammonium salt, one, two, three, or four of $R^1$, $R^2$, $R^3$, and $R^4$ of Formula III, or one, two, three of $R^6$, $R^7$, and $R^1$ of Formula IV are independently selected from carbon-containing group(s) that are linear or branched C1-C12 alkyl groups, linear or branched C1-C8 alkyl groups, or linear or branched C1-C6 alkyl groups. Exemplary alkyl groups include:
methyl,
ethyl,
propyl, isopropyl,
butyl, isobutyl, sec-butyl, tert-butyl,
pentyl, cyclopentyl, isopentyl, neopentyl,
hexyl, cyclohexyl, 1-, 2-, and 3-methylbutyl, 1,1-, 1,2-, or 2,2-dimethylpropyl, 1-ethyl-propyl, 1-, 2-, 3-, or 4-methylpentyl, 1,1-, 1,2-, 1,3-, 2,2-, 2,3-, or 3,3-dimethylbutyl, 1- or 2-ethylbutyl, 1-ethyl-1-methylpropyl, and 1,1,2- or 1,2,2-trimethylpropyl, methylcyclopentyl;
heptyl, 2-methylhexyl, 3-methylhexyl, 4-methylhexyl, 5-methylhexyl, 3-ethylpentyl, 2,2,3-trimethylbutyl, 2,2-dimethylpentyl, 2,3-dimethylpentyl, 2,4-dimethylpentyl, 3,3-dimethylpentyl, 3,4-dimethylpentyl, 4,4-dimethylpentyl, cycloheptyl, 1-methylcyclohexyl, and 2-methylcyclohexyl;
octyl, 2-methylheptyl 3-methylheptyl, 4-methylheptyl, 2-ethylhexyl, 3-ethylhexyl, 4-ethylhexyl, 5-ethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3-ethyl-2-methylpentyl, 3-ethyl-3-methylpentyl, 2,2,3-trimethylpentyl, 2,2,4-trimethylpentyl, 2,3,3-trimethylpentyl, 2,3,4-trimethylpentyl, and 2,2,3,3-tetramethylbutyl; and
nonyl, decyl, undecyl, and dodecyl.

In some embodiments one, two, three of $R^1$, $R^2$, $R^3$, and $R^4$ of Formula III, or one, two, three of $R^6$, $R^7$, and $R^8$ of Formula IV are independently selected from methyl, ethyl, propyl, isopropyl, n-butyl, isobutyl, sec-butyl, and tert-butyl.

In some embodiments, in the ammonium salt, one, two, three, or four of $R^1$, $R^2$, $R^3$, and $R^4$ of Formula III, or one, two, three of $R^6$, $R^7$, and $R^8$ of Formula IV is/are hydroxyl.

In some embodiments, in the ammonium salt cation of Formula III, one of $R^1$, $R^2$, $R^3$, and $R^4$ is hydroxyl and two or three of $R^1$, $R^2$, $R^3$, and $R^4$ are linear or branched C1-C6 hydroxyalkyl or hydroxyaryl groups, or are linear or branched C1-C6 alkyl groups. In some embodiments, in the ammonium salt cation of Formula IV, one of $R^6$, $R^7$, and $R^8$ of is hydroxyl, and one or two of $R^6$, $R^7$, and $R^8$ is/are linear or branched C1-C6 hydroxyalkyl groups or is/are linear or branched C1-C6 alkyl groups or aryl groups. Exemplary hydroxyalkyl groups include hydroxymethyl, 1- or 2-hydroxyethyl, 1-, 2-, or 3-hydroxypropyl, 2-hydroxyisopropyl, 1-, 2-, 3-, or 4-hydroxybutyl, and 1-, 2-, or 3-hydroxyisobutyl; or are linear or branched C1-C6 alkyl groups, such as methyl, ethyl, propyl, isopropyl, butyl, isobutyl, sec-butyl, or tert-butyl.

Some exemplary cations of ammonium salts having a hydroxyl group and two hydroxyalkyl groups, include, but are not limited to di(hydroxyethyl)-hydroxylammonium and di(hydroxypropyl)-hydroxylammonium, or having a hydroxyl group and two hydroxyaryl groups include N,N-bis(2-hydroxyphenyl)hydroxyl ammonium, N,N-bis(4-hydroxyphenyl)hydroxyl ammonium, which are shown below. An exemplary cation of an ammonium salt having a hydroxylated alkyl aryl group is di(2-hydroxy, 2-phenylethyl)-hydroxylammonium, shown below.

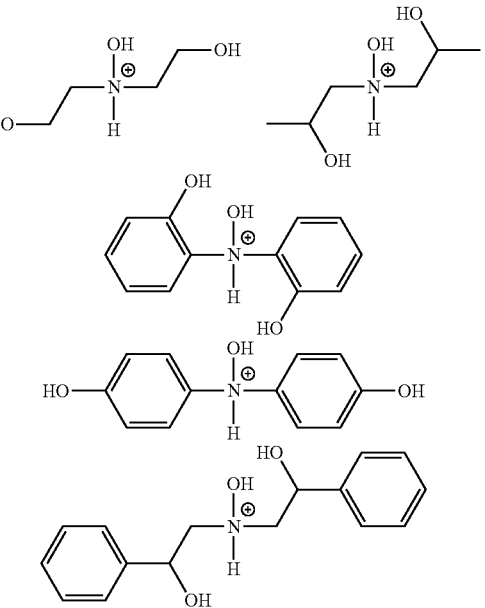

Some exemplary cations of ammonium salts having a hydroxyl group and two alkyl groups, include, but are not limited to diethylhydroxylamine and dipropylhydroxylamine. An exemplary cation of an ammonium salt having a hydroxyl group and two aryl groups, include, but are not limited to N,N-dibenzylhydroxylammonium, Structures are shown below.

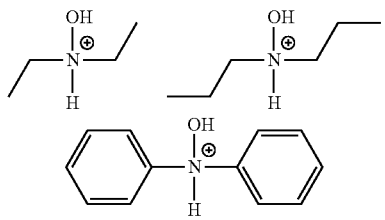

In some embodiments, in the ammonium salt, one, two, three, or four of $R^1$, $R^2$, $R^3$, and $R^4$ of Formula III, or one, two, three of $R^6$, $R^7$, and $R^8$ of Formula IV is/are hydroxyl.

In some embodiments of Formula III the oxygen- and carbon-containing group is selected from the group consisting of 2-benzoxazolyl, adipyl, glutaryl, succinyl, malonyl, acetyl, acrylyl, methacrylyl, caproyl, benzoyl, phthaloyl, terephthaloyl, carbethoxy, carbonyl, and formyl. In some embodiments of Formula III the carbon-containing group is a nitrogen- and carbon-containing group, such as selected from the group consisting of 1,3,5-sym-triazinyl, 2-benzimidazolyl, 2-pyridyl, and 2-pyrazinyl. In some embodiments of Formula III the carbon- and oxygen-containing group is a nitrogen-, oxygen-, and carbon-containing group, such as selected from the group consisting of 2-pyrimidinyl and aminocarbonyl. In some embodiments of Formula III the carbon-containing group is an oxygen-sulfur- and carbon-containing group, such as 3-mercaptopropionyl In some embodiment, the ammonium salt includes a cation of Formula IV as described herein:

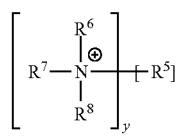

and is more specifically a cation of the Formula VI:

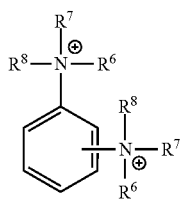

wherein $R^6$, $R^7$, and $R^8$ are independently selected from (a) —H, (b) a carbon-containing group, (c) an oxygen-containing group, (d) an oxygen- and carbon-containing group. In some embodiments at least one of $R^6$, $R^7$, and $R^8$ is a linear or branched C1-C12 alkyl groups, an aryl group, or a C1-C12 arylalkyl group.

Some exemplary cations of phenylenediammonium salts include N,N'-di-sec-butylphenylenediammonium, N-sec-butyl-N'-phenylphenylenediammonium, N,N'-di-phenylphenylenediammonium, N-1,3-dimethylbutyl-N'-phenyl-p-phenylenediammonium, and N-1,4-dimethylpentyl-N'-phenyl-p-phenylenediammonium, which are shown below.

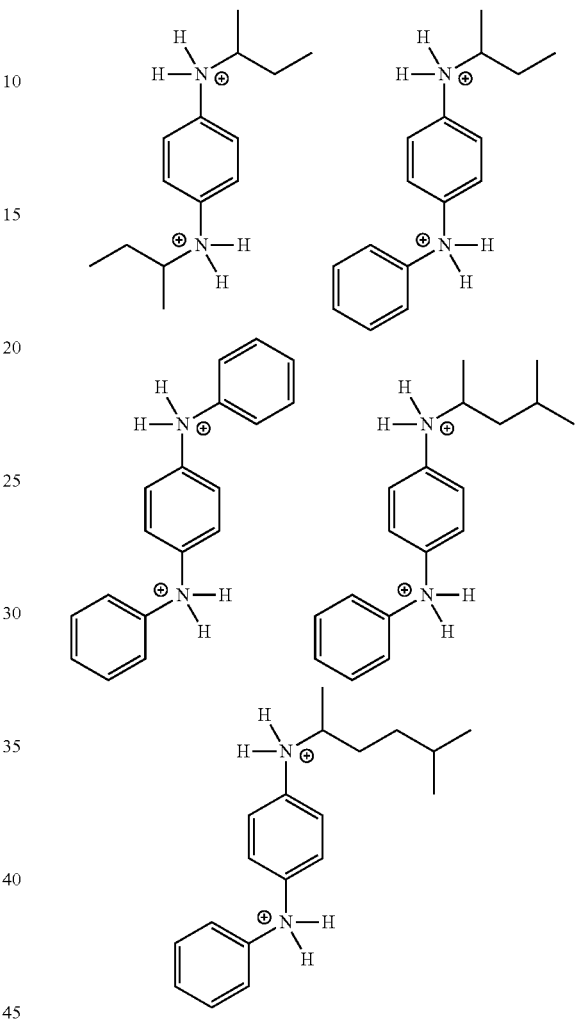

The cation of the ammonium salt can optionally be described with reference to the number and type of atoms in the cation. In embodiments, the cation of the ammonium salt has (a) an amount of nitrogen atoms in the range of 1-4, or preferably 1 or 2, (b) an amount of carbon atoms in the range of 0-18, 1-12, or 2-10; (c) an amount of oxygen atoms in the range of 0-6, 1-4, or 1-3; (d) an amount of hydrogen atoms in the range of 4-40, 6-30, or 8-24; or any combination of (a)-(d).

In some preferred embodiments, the cation of the ammonium salt has (a) one or two nitrogen atom(s), (b) an amount of carbon atoms in the range of 6-12; (c) an amount of oxygen atoms in the range of 2-5; and (d) an amount of hydrogen atoms in the range of 16-28. In some preferred embodiments, the cation of the ammonium salt has (a) one or two nitrogen atom(s) and (b) an amount of carbon atoms in the range of 8-10; (c) an amount of oxygen atoms in the range of 3-4; and (d) an amount of hydrogen atoms in the range of 19-25.

In other preferred embodiments, the cation of the ammonium salt has a nitrogen atom and (a) an amount of carbon atoms in the range of 2-6; (b) one, two, or no oxygen atoms; and (c) an amount of hydrogen atoms in the range of 8-16. In some preferred embodiments, the cation of the ammonium salt has a nitrogen atom and (a) an amount of carbon atoms in the range of 3-5; (b) one oxygen atom; and (c) an amount of hydrogen atoms in the range of 10-14.

In preferred embodiments of Formula III, one or two of $R^1$, $R^2$, $R^3$, and $R^4$ are —H, and one or two of $R^6$, $R^7$, and $R^8$ of Formula IV are —H.

The ammonium salt can optionally be based on a mixture of different cations, such a mixture of different cations according to general Formula III and/or IV described herein. Therefore, in a composition or method using the quinone methide polymerization retarder, there can be two or more different cationic species of Formula III and/or IV forming two or more different ammonium salts.

In embodiments, the ammonium salt comprises an anion that includes a carboxylate group, a sulfonate group, a phosphonate group, a nitrate group, a nitrite group, or a combination thereof. Other anions for the ammonium salt include aldonates, aldarates, ulosonates, and uronate carboxylates of sugar acids. Some preferred anions include a carboxylate group, such as found in gluconate. Another exemplary anion is ascorbate.

The cation of the ammonium salt can be an organic anion that includes a desired amount of carbon atoms. In embodiments, the organic anion has an amount of carbon atoms in the range of 2-18, 3-12, or 4-10. The organic anion can also have a desired amount of oxygen atoms, such as 2, 3, or 4.

In embodiments, the organic anion of the ammonium salt can be a carboxylate-containing anion that is selected from the group consisting of acetate (ethanoate);

propionate (propanoate);

butyrate (butanoate), isobutyrate (2-methylpropanoate);

valerate (pentanoate), isovalerate (3-methylbutanoate), 2-methylbutanoate, pivalate (2,2-dimethylpropanoate);

caproate (hexanoate), 2-methylvalerate, 3-methylvalerate, 4-methylvalerate, 2,2-2,2-dimethylbutanoate, 2-ethylbutanoate;

heptanoate (enanthoate), 2-methylcaproate, 3-methylcaproate, 4-methylcaproate, 5-methylcaproate, 2,2-dimethylvalerate, 2-ethylvalerate;

caprylate (octanoate), 2-methylheptanoate, 3-methylheptanoate, 4-methyl heptanoate, 5-methylheptanoate, 6-methylheptanoate, 2,2-dimethylcaproate, 2-ethylcaproate (2-ethylhexanoate), and 2-propylvalerate.

The ammonium salt can optionally be based on a mixture of different anions, such a mixture of different carboxylate-containing anions as described herein. Therefore, in a composition or method using the quinone methide polymerization retarder, there can be two or more different anionic species forming two or more different ammonium salts.

The ammonium salt can optionally be described with reference to molar mass, such as a molar mass limit or a molar mass range. The ammonium salt can be of any desired molecular mass, such as suitable for use with the quinone methide in an antipolymerant composition or method.

In embodiments, the ammonium salt has a molar mass of less than about 1000 g/mol, less than 900 g/mol, less than 800 g/mol, less than 700 g/mol, less than 600 g/mol, less than 500 g/mol, less than 450 g/mol, less than 400 g/mol, less than 375 g/mol, or less than 350 g/mol. In embodiments, the ammonium salt has a molar mass of about 120 g/mol or greater, about 130 g/mol or greater, about 140 g/mol or greater, or about 150 g/mol or greater. Molar mass ranges of the disclosure can be based on any two of the lower and upper limits described herein (e.g., in the range of about 120 g/mol to about 1000 g/mol, etc.).

In other embodiments, the ammonium salt can have has a molar mass of greater than about 1000 g/mol. For example, a high molecular weight ammonium salt can be in the form of a polymeric ammonium salt. Polymeric ammonium salts, including polymeric quaternary ammonium salts, are known in the art. See, for example, U.S. Pat. Nos. 2,595,225, 4,247,476, and U.S. Application Pub. No. 2006/0062753.

In some modes of practice, the ammonium salt is formed by reaction of an amine reactant compound with an acid. Reaction results in protonation of the nitrogen atom of the amine reactant compound forming the amine cation, and the anion of the deprotonated acid. Reaction of the amine reactant compound with the acid be carried out in a solvent, or in neat form (i.e., only with the amine compound and acid).

In some modes of practice, solvents used for reaction of the amine compound with the acid include polar aprotic solvents. Exemplary polar aprotic solvents include ethyl acetate, dichloromethane (DCM), tetrahydrofuran (THF), dimethylformamide (DMF), dimethylsulfoxide (DMSO), acetone, and hexamethylphosphoric triamide (HMPT).

Exemplary amine reactant compounds are of Formula VII: $NR^9R^{10}R^{11}$, wherein $R^9$, $R^{10}$, and $R^{11}$, are independently selected from (a) a carbon-containing group, (b) an oxygen-containing group, (c) an oxygen- and carbon-containing group In embodiments, (a) the carbon-containing group can consist of carbon, oxygen, and hydrogen, (b) the oxygen-containing group can consists of oxygen and hydrogen, (c) the oxygen- and carbon-containing group can consists of carbon, oxygen, and hydrogen, or any combination of (a)-(c). Exemplary groups that include oxygen atom(s) can include chemistries such as hydroxyl, carbonyl, ester, and ether. In embodiments, one or more of $R^9$, $R^{10}$, and $R^{11}$, has one oxygen-containing group selected from hydroxyl, carbonyl, ester, and ether. In embodiments, one or more of $R^9$, $R^{10}$, and $R^{11}$ has two or three oxygen-containing groups selected from hydroxyl, carbonyl, ester, and ether, or a combination thereof.

In some embodiments, in the amine reactant compound, one, two, or three of $R^9$, $R^{10}$ and $R^{11}$ are independently selected from oxygen- and carbon-containing group(s) that are linear or branched C1-C12 alkoxy groups, linear or branched C1-C8 alkoxy groups, or linear or branched C1-C6 alkoxy groups. Exemplary alkoxy groups such as methoxy, ethoxy, iso-proproxy, etc., are discussed with reference to $R^1$, $R^2$, $R^3$, and $R^4$ groups of Formula III, and can be used for any one or more of $R^9$, $R^{10}$, and $R^{11}$.

In some embodiments, in the amine reactant compound, one, two, or three of $R^9$, $R^{10}$ and $R^{11}$ are independently selected from carbon-containing group(s) that are linear or branched C1-C12 alkyl groups, linear or branched C1-C8 alkyl groups, or linear or branched C1-C6 alkyl groups. Exemplary alkyl groups such as methyl, ethyl, propyl, isopropyl, butyl, isobutyl, sec-butyl, tert-butyl, etc., are discussed with reference to $R^1$, $R^2$, $R^3$, and $R^4$ groups of Formula III, and can be used for any one or more of $R^9$, $R^{10}$, and $R^{11}$.

In some embodiments, in the amine reactant compound, one, two, or three of $R^9$, $R^{10}$ and $R^{11}$ are hydroxyl (—OH).

Exemplary amine reactant compounds include trialkanolamines (trisalkanolamines) such as triethanolamine (TEA), triisopropanolamine (TIPA), tributanolamine, N,N-bis(2-hydroxyethyl)-N-(2-hydroxypropyl)amine (DEIPA), N,N-bis (2-hydroxypropyl)-N-(hydroxyethyl)amine (EDIPA), tris(2-hydroxybutyl)amine, hydroxyethyl di(hydroxypropyl)

amine, hydroxypropyl di(hydroxyethyl)amine, tri(hydroxypropyl)amine, hydroxyethyl di(hydroxy-n-butyl)amine, hydroxybutyl di(hydroxypropyl)amine, and combinations thereof.

Other exemplary amine reactant compounds include dialkanolalkylamines (monoalkyldialkanolamine) such as N,N-bis(2-hydroxyethyl)ethylamine, methyldi-ethanolamine, methyldiisopropanolamine (MDIPA), N-propyldiethanolamine, N-butyldiethanolamine, and N-methyldipropanolamine.

Other exemplary amine reactant compounds include dialkylalkanolamines (monoalkanoldialkylamine) such as N,N-diethylisopropanolamine (diethylamino-propanol), N,N-diethylethanolamine (diethylaminoethanol), N-(2-hydroxyethyl) dimethylamine (dimethylethanolamine), and dimethylpropanolamine.

Other exemplary amine reactant compounds include dialkylhydroxylamines such as dimethylhydroxylamine, N,N-diethylhydroxylamine, dipropylhydroxyl-amine, N,N-diisopropylhydroxylamine, N,N-dibutylhydroxylamine, N,N-diiso-butylhydroxylamine dipentylhydroxylamine, N,N-dihexylhydroxylamine, and N,N-di(4-methylpentyl) hydroxylamine.

Other exemplary amine reactant compounds include dialkanolhydroxyl-amines such as diethanolhydroxylamine.

For preparation of compounds including the cation of Formula IV, exemplary amine reactant compounds (e.g., which can be used to make phenylenediammonium-based compounds) include alkyl and/or aryl-derivatives of ortho-phenylenediamine and para-phenylenediamine compounds such as N,N'-dimethyl-o-phenylenediamine, N,N'-dimethyl-p-phenylenediamine, N,N'-diethyl-p-phenylenediamine, N,N'-di-sec-butyl-p-phenylenediamine; N-methyl-N'-phenyl-p-phenylenediamine, N-ethyl-N'-phenyl-p-phenylenediamine, N-phenyl-N'-propyl-p-phenylenediamine, N-butyl-N'-phenyl-p-phenylenediamine, N-phenyl-N'-sec-butyl-p-phenylenediamine, N-isopropyl-N'-phenyl-p-phenylenediamine, N-isobutyl-N'-phenyl-p-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-(1-methylhexyl)-N'-phenyl-p-phenylenediamine, N-(1,3-dimethylbutyl)-N'-phenyl-p-phenylenediamine, and N-(1,4-dimethylpentyl)-N'-phenyl-p-phenylenediamine.

The ammonium salt can be prepared by reacting the amine reactant compound with an organic acid, such as a monofunctional carboxylic acid. Exemplary monofunctional carboxylic acids include acetic acid, propionic acid (propanoate); butyric acid, isobutyric acid; valeric acid, isovaleric acid, 2-methylbutanic acid, pivalic acid; capric acid, 2-methylvaleric acid, 3-methylvaleric acid, 4-methylvaleric acid, 2,2-2,2-dimethylbutanoic acid, 2-ethylbutanoic acid; heptanoic acid, 2-methylcaproic acid, 3-methylcaproic acid, 4-methylcaproic acid, 5-methylcaproic acid, 2,2-dimethylvaleric acid, 2-ethylvaleric acid; caprylic acid, 2-methylheptanoic acid, 3-methylheptanoic acid, 4-methyl heptanoic acid, 5-methylheptanoic acid, and 6-methylheptanoic acid. Other acids that can be reacted with the amine reactant compound include diacids (difunctional acids) as described herein.

The ammonium salt can be formed by reacting the amine reactant compound and monofunctional acid in equimolar or approximately equimolar amounts. Alternatively, if the acid is a difunctional acid, such as a dicarboxylic acid, the amine reactant cam be reacted with the diacid at a 2:1 molar ratio. Exemplary diacids include malonic acid, succinic acid, glutaric acid, adipic acid, pimelic acid, maleic acid, fumaric acid, suberic acid, azelaic acid, and sebacic acid.

In some modes of practice the ammonium salt is formed by reaction of an amine reactant and acid in the presence of a solvent or solvent mixture. Solvents that can be used for reaction of the amine compound with the acid include polar aprotic solvents. Exemplary polar aprotic solvents include ethyl acetate, dichloromethane (DCM), tetrahydrofuran (THF), dimethylformamide (DMF), dimethylsulfoxide (DMSO), acetone, and hexamethylphosphoric triamide (HMPT), and combinations thereof. Other solvents that can be used for reaction of the amine compound with the acid include aprotic solvents, such as aprotic hydrocarbon based solvents. Exemplary nonpolar aprotic solvents include toluene, cyclohexane, hexane, heptane, xylene, and carbon tetrachloride.

The amine reactant compound and acid can be present at desired concentrations in the solvent, the concentration selected to optimize reaction of the two components. In exemplary modes of practice the, amine reactant compound and acid together are present in an amount by weight of the solvent-based reaction composition in the range of about 5% (wt) to about 50% (wt), or about 15% (wt) to about 40% (wt). Reaction can be carried out at a desired temperature with agitation, such as promoted by using a magnetic stirrer.

After a desired period of reaction and formation of the ammonium salt, the reaction composition may exhibit an increase in viscosity. The solvent can then be removed using low pressure (e.g., by vacuum), optionally with heat. Depending on the type of amine reactant compound and acid used, following removal of the solvent, the ammonium salt can have the properties of a solid or properties of a (ionic) liquid.

In embodiments, the ammonium salt can be in the form of an ionic liquid at room temperature range, or at a temperature between room temperature and a temperature where the ammonium salt is used in combination with the quinone method to inhibit polymerization of monomers in a monomer-containing composition. In embodiments, ammonium salts of the disclosure are predicted to have a very high boiling point and therefore are expected to remain in liquid state at high temperature conditions (e.g., greater than 300° C., or greater than 400° C.) during monomer processing. In some cases, determination of whether the ammonium salt is an ionic liquid is determined at room temperature (about 25° C.).

The disclosure also provides compositions that include the quinone methide and the ammonium salt.

In some embodiments, the quinone methide polymerization retarder and the ammonium salt (with one or more optional components) are present in a composition with a solvent, or a combination of solvents. A solvent or solvent combination can be chosen so that one or more of the quinone methide polymerization retarder and the ammonium salt are soluble in the solvent or solvent combination. If the ammonium salt is a liquid at ambient conditions, a miscible solvent can be chosen. In embodiments, if ammonium salt is a liquid it may also function as a solvent, and can be used to at least partially solvate the quinone methide polymerization retarder.

Useful solvents include any solvent in which a combination of quinone methide polymerization retarder and the ammonium salt (and optionally inhibitor) are soluble or can be stably suspended. In some embodiments, a solvent or solvent combination can be selected from water soluble or water miscible solvents such glycol-based solvents and hydrophobic or hydrocarbon solvents such as aromatic solvents, paraffinic solvents, or mixtures of both.

Exemplary glycol solvents include, but are not limited, $C_1$-$C_8$ glycols such as ethylene glycol, propylene glycol, diethylene glycol, and triethylene glycol, ethers of such glycols such as diethylene glycol monobutyl ether, diethylene glycol monomethyl ether, diethylene glycol monoethyl ether, diethylene glycol monobutyl ether, triethylene glycol, triethylene glycol monomethyl ether, liquid polyethylene glycol, dipropylene glycol, dipropylene glycol monomethyl ether, dipropylene glycol monoethyl ether, and a low molecular weight polypropylene glycol and the like and combinations thereof. Commercial solvents such as Butyl Carbitol and Butyl CELLOSOLVE™, which contains primarily Butyl CARBITOL™, which consists primarily of ethylene glycol monobutyl ether may be used and are available from DOW.

Other exemplary hydrophobic or hydrocarbon solvents include heavy aromatic naphtha, toluene, ethylbenzene, isomeric hexanes, benzene, xylene, such as ortho-xylene, para-xylene, or meta-xylene, and mixtures of two or more thereof.

In some embodiments, the solvent is selected from glycol and aromatic naphtha and combinations thereof.

The amount of quinone methide polymerization retarder and the ammonium salt (with one or more optional components such as a polymerization inhibitor), in a solvent, or a combination of solvents, can be described one or more ways, such as by the percent solids (wt) of these components in the composition, or by the molar amount in the composition.

Compositions of the disclosure can be made using any desired method. For example, preparations of the quinone methide polymerization retarder and the ammonium salt (with one or more optional components), and optionally with solvent, can be obtained by a user, such as a commercial preparation, and then combined and stored, or alternatively added together, such as in a point of use procedure.

The ammonium salt when used in combination with the quinone methide retarder, can improve the antipolymerant efficacy of the retarder. For example, use of the ammonium salt in combination with the quinone methide retarder, can inhibit polymerization of monomers to a greater extent than use of the retarder alone, or the ammonium salt alone.

Amounts of the quinone methide polymerization retarder and the ammonium salt in a composition can be described in various ways, such as by a weight percentage (% wt.) of each component in the composition, or by molar amounts of the compounds. These compounds can also be described in terms of weight ratios, or in terms of relative amounts to one another, in a composition.

In some embodiments, in a composition the amount (either measured as % wt. or molar amount) of the quinone methide polymerization retarder is present in an amount greater than the amount of the ammonium salt. For example, the amount of the quinone methide polymerization retarder can be greater than about 1.5×, greater than about 2×, greater than about 2.5×, greater than about 3×, greater than about 3.5×, greater than about 4×, greater than about 4.5×, or greater than about 5×, than the amount (% wt. or molar amount) of the ammonium salt in a composition. As another example, the amount of quinone methide polymerization retarder is in the range of about 1.5× to about 1000×, 1.5× to about 250×, 1.5× to about 100×, or about 1.5× to about 50×, or about 1.5× to about 25×, or about 1.5× to about 15×, or greater than the amount (% wt. or molar amount) of the ammonium salt in the composition.

The amounts of quinone methide and the ammonium salt in composition can optionally be described in terms of the molar ratio to one another. In embodiments, the quinone methide and the ammonium salt are present in a molar ratio in the range of greater than 1:1 to about 1000:1, greater than 1:1 to about 250:1, greater than 1:1 to about 100:1, greater than 1:1 to about 50:1, greater than 1:1 to about 25:1, greater than 1:1 to about 20:1, or greater than 1:1 to about 15:1, respectively.

A composition with predetermined amounts of quinone methide polymerization retarder and ammonium salt can be prepared so that when the composition is added to a monomer composition, or composition capable for forming monomer, both the quinone methide polymerization retarder and ammonium salt are at working concentrations in the monomer composition. Various working ranges of the quinone methide polymerization retarder and ammonium salt are described herein.

Optionally, a polymerization inhibitor, such as one capable for forming a stable nitroxide group, may be used in small amounts with the quinone methide polymerization retarder and the ammonium salt, or may be entirely excluded from the composition.

A "polymerization inhibitor," in the presence of polymerizable monomers, inhibits the formation of a polymer from those monomers during an induction time. After the induction time has lapsed, the polymer's formation occurs at substantially the same rate that it would form at in the absence of the polymerization inhibitor.

A "polymerization retarder," such as quinone methide compounds disclosed herein, does not exhibit an induction time, but instead once added to a polymerizable monomer composition reduces the rate at which the formation of the polymer occurs relative to the rate at which it would have formed in the absence of the composition of matter.

Polymerization inhibitors, as opposed to polymerization retarders, are generally consumed rapidly. Polymerization retarders, while they slow down the rate of polymerization reactions, are generally not as effective as polymerization inhibitors. Polymerization retarders, however, are usually not consumed as quickly as polymerization inhibitors.

Polymerization inhibitors and polymerization retarders can be considered generally as "antipolymerants" which are compounds that can inhibit or reduce the formation of polymers from one or more radically polymerizable compounds.

Exemplary polymerization inhibitors that can be used in small amounts, or can be completely excluded from the composition, and that have an N to O bond include nitroxide-, amine oxide-, hydroxylamine-, nitro-, nitroso-, and nitrone-containing compounds. For example, in a composition comprising polymerizable monomer, the quinone methide, and the ammonium salt, a nitroxyl group containing antipolymerant can optionally be present in an amount of less than 50 ppm, less than 25 ppm, less than 10 ppm, less than 5 ppm, less than 2.5 ppm, less than 2 ppm, less than 1.5 ppm, less than 1 ppm, less than 0.75 ppm, or less than 0.5 ppm, or can be excluded from the composition altogether.

For example, in a composition comprising polymerizable monomer and the nitrogen- and oxygen-containing aromatic antipolymerant, a nitroxyl group containing antipolymerant can optionally be present in an amount of less than 50 ppm, less than 25 ppm, less than 10 ppm, less than 5 ppm, less than 2.5 ppm, less than 2 ppm, less than 1.5 ppm, less than 1 ppm, less than 0.75 ppm, or less than 0.5 ppm.

Exemplary nitroxide-containing polymerization inhibitors that can be used in small amounts, or that can be completely excluded from the composition, include, but are not limited to: 2,2,6,6-tetramethylpiperidinyl-1-oxyl (TEMPO), 4-hydroxy-2,2,6,6-tetramethylpiperidinyl-1-oxyl (HTMPO), 4-oxo-2,2,6,6-tetramethylpiperidinyl-1-oxyl (OTEMPO), 1-hydroxy-2,2,6,6-tetramethylpiperidine (TEMPOH), 1,4-dihydroxy-2,2,6,6-tetramethylpiperidine (HTMPOH), and 1-hydroxy-4-oxo-2,2,6,6-tetramethylpiperidine (OTEMPOH), N,N-diethylhydroxylamine, and N-isopropylhydroxylamine, di-tert-butyl nitroxyl, 1-oxyl-2,2,6,6-tetramethyl-4-n-propoxypiperidine, 1-oxyl-2,2,6,6-tetramethyl-4-n-butoxypiperidine, 1-oxyl-2,2,6,6-tetramethyl-4-t-butoxypiperidine, 1-oxyl-2,2,6,6-tetramethyl-4-s-butoxypiperidine, 1-oxyl-2,2,6,6-tetramethyl-4-(2-methoxyethoxy) piperidine, 1-oxyl-2,2,6,6-tetramethyl-4-(2-methoxyethoxyacetoxy)piperidine, 1-oxyl-2,2,6,6-tetramethylpiperidin-4-yl stearate, 1-oxyl-2,2,6,6-tetramethylpiperidin-4-yl acetate, 1-oxyl-2,2,6,6-tetramethylpiperidin-4-yl butyrate, 1-oxyl-2,2,6,6-tetramethylpiperidin-4-yl 2-ethylhexanoate, 1-oxyl-2,2,6,6-tetramethylpiperidin-4-yl octanoate, 1-oxyl-2,2,6,6-tetramethylpiperidin-4-yl laurate, 1-oxyl-2,2,6,6-tetramethylpiperidin-4-yl benzoate, 1-oxyl-2,2,6,6-tetramethylpiperidin-4-yl 4-tert-butylbenzoate, 1-oxyl-2,2,6,6-tetramethyl-4-allyloxy-piperidine, 1-oxyl-2,2,6,6-tetramethyl-4-acetamidopiperidine, 1-oxyl-2,2,6,6-tetramethyl-4-(N-butylformamido)piperidine, N-(1-oxyl-2,2,6,6-tetramethylpiperidin-4-yl)-caprolactam, N-(1-oxyl-2,2,6,6-tetramethylpiperidin-4-yl)-dodecylsuccinimide, 1-oxyl-2,2,6,6-tetramethyl-4-(2,3-dihydroxypropoxy)piperidine, 1-oxyl-2,2,6,6-tetramethyl-4-(2-hydroxyl-4-oxapentoxy)piperidine, and mixtures thereof. (See, for example, U.S. Pat. No. 9,266,797.) Any of these compounds can be present at very low amounts (less than 50 ppm, 25 ppm, 10 ppm, etc., as described herein) in a polymerizable monomer composition, or can be excluded from the composition altogether.

Other exemplary nitroxide-containing polymerization inhibitors that can be used in small amounts, or that can be completely excluded from the composition, include bis-nitroxide and tris-nitroxide polymerization inhibitors such as bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethyl-piperidin-4-yl) n-butylmalonate, bis(1-oxyl-2,2,6,6-tetramethylpiperidin-4-yl) phthalate, bis (1-oxyl-2,2,6,6-tetramethylpiperidin-4-yl) isophthalate, bis (1-oxyl-2,2,6,6-tetramethylpiperidin-4-yl) terephthalate, bis (1-oxyl-2,2,6,6-tetramethylpiperidin-4-yl) hexahydroterephthalate, N,N'-bis(1-oxyl-2,2,6,6-tetramethylpiperidin-4-yl) adipamide, 2,4,6-tris-[N-butyl-N-(1-oxyl-2,266-tetramethylpiperidin-4-yl)]-s-triazine, 2,4,6-tris-[N-(1-oxyl-2,2,6,6-tetramethylpiperidin-4-yl)]-s-triazine, 4,4'-ethylenebis(1-oxyl-2,2,6,6-tetramethylpiperazin-3-one), and mixtures thereof (See, for example, U.S. Pat. No. 9,266,797.) Any of these compounds can be present at very low amounts (less than 50 ppm, 25 ppm, 10 ppm, etc., as described herein) in a polymerizable monomer composition, or can be excluded from the composition altogether.

Optionally, a composition including the quinone methide polymerization retarder and the ammonium salt of the disclosure can further include a stabilizer compound that is a primary amine, such as $R^1NH_2$, wherein $R^1$ is a linear, branched, or cyclic alkyl group of 4-24, 6-24, or 8-24 carbons, or a stabilizer that is a secondary amine, such as $R^2NHR^3$, wherein $R^2$ and $R^3$ are independently selected from linear, branched, or cyclic alkyl group of 1-23 carbon atoms with the proviso that the total number of carbon atoms in $R^2$ and $R^3$ is in the range of 4-24, 6-24, or 8-24 carbons, as disclosed in U.S. Application Pub. No. 2020/0017610 (Masere et al.).

Methods of inhibiting the polymerization of monomers in a monomer-containing composition can be carried out by adding the components of the quinone methide polymerization retarder and the ammonium salt (with one or more optional components) to a composition that includes a polymerizable monomer. The quinone methide can be added to the monomer composition at the same time as the ammonium salt, before addition of the ammonium salt, or after addition of the ammonium salt, or any combination thereof. The manner of adding the quinone methide and the ammonium salt can be carried out to provide desired concentrations of these compounds in the monomer composition at any one or more points during the treatment process.

The quinone methide polymerization retarder inhibits polymerization of the polymerizable monomer, and the presence of the ammonium salt improves the efficacy of the quinone methide polymerization retarder.

The polymerizable monomer that is subjected to polymerization retardation can include a vinyl or ethylenically unsaturated group. For example, the components of the quinone methide and ammonium salt can be added to a composition that includes one or more of the following polymerizable monomers: acrolein, acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyl acetate, vinyltoluene, and vinylpyridine.

The polymerizable monomer can be present in a crude mixture of compounds, a semi-refined mixture of compounds, or a fully-refined mixture of compounds. For example, the components of the quinone methide polymerization retarder and the ammonium salt may be added to a process stream that includes the polymerizable monomer. In methods, the components can be added before, during, or after, (or combinations thereof) a processing step, such as distillation, wherein compounds in the composition are separated from one another. The components can inhibit polymerization of monomer at any one or more stages in a processing system, and therefore reduce or prevent fouling of equipment.

Alternatively, the components of the quinone methide polymerization retarder and the ammonium salt may be added to a process stream that includes a compound capable of forming into a polymerizable monomer (e.g., a monomer precursor). For example, in compositions including a compound that is capable of forming a polymerizable monomer as an unwanted by-product, the presence of the quinone methide polymerization retarder and the ammonium salt can inhibit polymerization of the monomer if it does form as a by-product, and can therefore reduce or prevent fouling of equipment.

In some modes of practice, the quinone methide polymerization retarder and the ammonium salt are introduced into a monomer-containing composition to provide a desired amount of each reagent in the composition. The quinone methide polymerization retarder and the ammonium salt can be introduced simultaneously, such as delivered from a composition where the components are in mixture, or can be delivered individually or partially combined either sequentially, or in an overlapping manner. The resulting introduction of the components into the monomer-containing composition can provide the quinone methide polymerization retarder and the ammonium salt at desired concentrations.

For example, at a polymerizable monomer concentration in the range of 0.05 to 50000 ppm, the quinone methide polymerization retarder can be introduced to provide an amount of retarder in the range of 125 to 250 ppm, and the ammonium salt can be introduced to provide an amount of ammonium salt in the range of 5 to 25 ppm. And as another example, the quinone methide polymerization retarder can be introduced to provide an amount of retarder in the range of 150 to 225 ppm, and the and the ammonium salt can be introduced to provide an amount of ammonium salt in the range of 12 to 20 ppm.

In some modes of practice the quinone methide polymerization retarder and the ammonium salt are optionally used in a process along with a polymerization inhibitor, such as a nitroxide-containing polymerization inhibitor (e.g., HTEMPO, etc.), preferably at low amounts, or the nitroxide-containing polymerization inhibitor can be eliminated from the process entirely. For example, in some modes of practice, a polymerization inhibitor is added to a polymerizable monomer composition, such as a process stream, prior to adding the quinone methide polymerization retarder and the ammonium salt. The polymerization inhibitor can be added over a period of time and then the quinone methide polymerization retarder and the ammonium salt can be added after the period (i.e., sequentially), or the addition of polymerization inhibitor, quinone methide polymerization retarder, and the ammonium salt to the polymerizable monomer composition, can be overlapping. In other modes of practice, the polymerization inhibitor, quinone methide polymerization retarder, and the ammonium salt can be added simultaneously to a polymerizable monomer composition. The use of the quinone methide and ammonium salt can significantly reduce the amount of polymerization inhibitor in the monomer composition.

The term "fouling" refers to the formation of polymers, prepolymers, oligomer and/or other materials which would become insoluble in and/or precipitate from a stream and deposit on equipment under the conditions of operation of the equipment. In turn, the quinone methide polymerization retarder which is enhanced by the ammonium salt, can be referred to as "antifouling" as they prevent or reduce such formation.

Optionally, the ability of the compositions of the disclosure to inhibit polymerization can be described relative to a composition that does not include the ammonium salt. The effect of the ammonium salt can be understood by measuring the formation of a polymer (e.g., polystyrene) in a monomer (e.g., styrene) composition over time, in the presence of a composition that includes quinone methide polymerization retarder and ammonium salt one with the retarder but without the ammonium salt (comparative). For example, a composition of the disclosure with quinone methide polymerization retarder and the ammonium salt improves inhibition of polymerization of the monomer by more than about 1.2 fold, more than about 1.4 fold, more than about 1.4 fold, more than about 1.5 fold, more than about 2 fold, more than about 3 fold, more than about 4 fold, more than about 5 fold, more than about 6 fold, more than about 7 fold, more than about 8 fold, more than about 9 fold, and in some cases even more than about 10 fold, as compared to a composition with quinone methide polymerization retarder but without the ammonium salt under the same conditions.

With reference to the combinations of exemplary quinone methides (QMCinn, QMPh) and exemplary ammonium salts (TIPA-2-EH, DIHA-2-EH) and experimental studies described herein, the combinations provided improved antipolymerant activity over composition having the quinone methide alone, and even improved antipolymerant activity over the nitro-group containing antipolymerant DNBP. The improvement was seen throughout the course of the antipolymerant test period.

The combinations provided improved antipolymerant activity over QMCinn alone over most time points tested, and the improvement became more pronounced over time, with the QMCinn and TIPA-2-EH combination showing greater than a six-fold improvement over QMCinn at the last time point (120 mins), even with QMCinn being used at a lower concentration. QMCinn and TIPA-2-EH combination also performed better than the nitro-group containing antipolymerant DNBP at most time points measured.

The components of the quinone methide polymerization retarder and the ammonium salt (and any other optional component) can be used in conjunction with compositions containing polymerizable monomers and "process equipment" such as reactors, reactor beds, pipes, valves, distillation columns, trays, condensers, heat exchangers, compressors, fans, impellers, pumps, recirculators, inter-coolers, sensors, and the like, that are associated with the process and which may be subject to fouling by monomer polymerization. This term also includes sets of these components where more than one of the components is part of a "system."

In one preferred method of use, a composition of the disclosure with quinone methide polymerization retarder and the ammonium salt and solvent (e.g., glycol) is used with a process that involves a distillation tower that is used to separate and purify vinylic monomers, such as styrene. For example, in art-known processes ethylbenzene can be subjected to a catalytic dehydrogenation reaction which results in the formation of styrene. The reaction product containing styrene also contains other compounds such as aromatics like toluene and benzene, unreacted ethylbenzene, and other materials such as polymers. This mixture of compounds is generally fractionally distilled using one or more distillations towers. Typically, heat is used to help separate the components in the distillation tower. Following distillation the fractionated components can be separated into pure product streams with higher purity. Optionally, the quinone methide polymerization retarder and the ammonium salt are used along with a polymerization inhibitor, such as a nitroxide-containing polymerization inhibitor (e.g., HTEMPO, etc.), in a distillation tower that is used to separate and purify vinylic monomers.

The quinone methide polymerization retarder and the ammonium salt-containing composition can be introduced into a stream leading from the reaction bed to the distillation tower, or can be directly added to the distillation tower. The compositions can be added prior to heating the monomer composition or while heating the monomer composition in the distillation tower. In embodiments, the ammonium salt has a boiling point that is higher than that of the desired compound or distillate (e.g., a monomer such as styrene) subject to distillation tower and during the distillation process the desired compound is separated from the ammonium salt by virtue of temperature difference. In embodiments, the boiling point difference between the compound of interest and the ammonium salt is about 10° C. or greater, about 15° C. or greater, about 20° C. or greater, about 25° C. or greater, about 30° C. or greater, about 35° C. or greater, about 40° C. or greater, about 45° C. or greater, or about 50° C. or greater.

Alternatively, or in addition to adding the quinone methide polymerization retarder and the ammonium salt-containing composition during the distillation process, the composition can be optionally or further added to a distillation effluent stream, such as a purified styrene stream.

Optionally, a nitroxide-containing polymerization inhibitor (e.g., HTEMPO, etc.), can be added to a distillation effluent stream prior to or along with the quinone methide polymerization retarder and the ammonium salt.

The quinone methide polymerization retarder and the ammonium salt, and optionally along with one or more other components, can be used with any "hydrocarbon process stream" which can include unsaturated monomer in order to stabilize the stream during transportation and storage. In some modes of practice, the components of the quinone methide polymerization retarder and the ammonium salt can be used in conjunction with a "petroleum product" which refers to any hydrocarbon product obtained from a subterranean reservoir, any product derived therefrom, or any mixture thereof. Polymerizable monomers are found in or can be chemically derived from petroleum products. Non-limiting examples of petroleum products include but are not limited to crude oil, reduced crude oil, crude distillate, heavy oil, or bitumen, hydrotreated oil, refined oil, byproducts of petroleum product processing such as pyrolysis, hydrotreating, or phase separation, or mixtures of two or more of these. A liquid petroleum product is a petroleum product that is substantially a liquid at 20° C.

The components of the quinone methide polymerization retarder and the ammonium salt can be added to or can be present in a "petroleum process stream" which refers to any petroleum product disposed within petroleum process equipment in fluid contact with an interior surface thereof The petroleum process stream can include, or can be capable of forming as a by-product, one or more polymerizable monomer. The process stream may be substantially static, such as a petroleum product disposed within in a settler (separator) or storage container for a selected period of contact, such as up to two years. The process stream may be substantially dynamic, such as a liquid petroleum product disposed within a pipe during transportation of the product from a first location to a second location. In some embodiments the process stream includes one or more additional components related to petroleum processing; such components are not particularly limited.

"Petroleum process equipment" or "petroleum process apparatus" refers to a man-made item having an interior surface including a metal, further wherein one or more petroleum products are fluidly contacted with the metal for any period of time and at any temperature further as determined by context. Petroleum process equipment includes items for removing petroleum products from a subterranean reservoir, for transporting one or more petroleum products from a first location to a second location, or for separating, refining, treating, isolating, distilling, reacting, metering, heating, cooling, or containing one or more petroleum products.

In embodiments, compositions including quinone methide polymerization retarder and the ammonium salt are thermally stable and have retarder activities in processing streams or other polymerizable monomer-containing compositions at temperatures of about 20° C. to about 400° C., for example about 100° C. to 400° C., or about 100° C. to 350° C., or about 100° C. to 300° C., or about 100° C. to 250° C., or about 100° C. to 200° C., or about 100° C. to 150° C.

In embodiments, compositions including quinone methide polymerization retarder and the ammonium salt can be introduced into a composition with a polymerizable monomer, such as a liquid petroleum process stream in a batch-wise, a continuous, or a semi-continuous manner. In some embodiments, the quinone methide polymerization retarder and the ammonium salt (and any other optional component) are introduced manually; and in other embodiments, their introduction is automated. In embodiments, the amount of the quinone methide polymerization retarder and the ammonium salt introduced over a selected unit of time is varied with a variable composition of the associated process stream. Such variability in dosing may be conducted manually by periodic testing of the process equipment interior surfaces, following by adjusting the amount of the composition up or down based on test results; or automatically by monitoring of one or more conditions within the interior of the petroleum process equipment and signaling the need to apply more composition to the process stream.

In some embodiments, the quinone methide polymerization retarder and the ammonium salt are added to a petroleum product that is a crude oil, a reduced crude oil, a heavy oil, a bitumen, a coker charge, a hydrotreater influent, a hydrotreater effluent, a flashed crude, a light cycle oil, or a diesel or naphtha refinery stream. In embodiments, the compounds are added to petroleum process equipment conventionally associated with the collecting, processing, transportation, or storage of one or more of crude oil, reduced crude oil, crude distillate, heavy oil, bitumen, coker charge, flashed crude, light cycle oil, or a diesel or naphtha refinery stream, including pipes and associated infrastructure used to fluidly connect process equipment items together to facilitate processing of a process stream disposed therein.

Equipment containing the polymerizable monomer-containing compositions that are treated with the quinone methide polymerization retarder and the ammonium salt and any other optional component can result in reduction or elimination of fouling interior surface of the equipment. In embodiments, fouling is measured as a relative increase in retention of solids within the treated composition compared to the retention of solids in untreated composition over the same time period. In embodiments, fouling is measured as a relative decrease in the weight or volume of precipitate arising from a selected period of contact of a treated process stream in an associated process equipment item, relative to the same period of contact of the process equipment with the corresponding untreated process stream. Stated differently, a reduction in fouling is a relative decrease in the measured weight or volume of solids deposited on or precipitated from process equipment contacted with the treated process stream over a selected period of time, when compared to the weight or volume of solids deposited or precipitated from an untreated process stream over the same period of time.

The quinone methide polymerization retarder and the ammonium salt can also inhibit unwanted polymerization and fouling of the process equipment in a primary fractionation process, light ends fractionation, non-aromatic halogenated vinyl fractionation and stabilization, process-gas compression, dilution steam system, caustic tower, quench water tower, quench water separator (pyrolysis gasoline), butadiene extraction, propane dehydrogenation, diesel and petrol fuel stabilization, olefin metathesis, styrene purification, hydroxyhydrocarbon purification, stabilization of vinylic monomers during transportation and storage, or delays the polymerization of resins and compositions comprising ethylenically unsaturated species.

The quinone methide polymerization retarder and the ammonium salt can be added at any given point in a process and at one or more locations. For example, such a composition can be added directly at the inter-coolers or compressors or upstream of the inter-coolers or compressors. The quinone methide polymerization retarder and the ammonium salt can be added continuously or intermittently to the process equipment as required preventing or reducing fouling.

The quinone methide retarder and ammonium salt can be introduced to desired systems by any suitable method. For example, it may be added in a neat or a dilute solution. In some embodiments, a composition containing the quinone methide polymerization retarder and the ammonium salt can be applied as a solution, emulsion, or dispersion that is sprayed, dripped, poured, or injected into a desired opening within a system or onto the process equipment or process condensate. In some embodiments, the composition may be added with a washoil or an attemperation water.

After introducing the composition to process equipment, treated process equipment can be observed to have less deposition on equipment than in process equipment without addition of the composition. Reduction or prevention in fouling can be evaluated by any known method or test. In some embodiments, the reduction or prevention of fouling can be accessed by measuring the time it takes for a sample with and without the antifoulant composition to gel. See the Experimental section for further details.

Example 1: Antipolymerant Activity of QMCinn (Comparative)

To test the ability antipolymerant compounds to inhibit the formation of polystyrene from a styrene monomer solution, stabilizer-free styrene was freshly prepared by removing the 4-tert-butylcatechol (TBC) immediately before using the styrene to prepare a solution of 0.679 mmolal of 7-cinnamyl quinone methide (QMCinn; 2,6-di-tert-butyl-4-(3-phenylallylidene)cyclohexa-2,5-dienone; U.S. Pat. No. 9,957,209) and styrene. In aliquots of 10 mL, the solution was transferred into twenty-four pressure tubes. After the removal of dissolved oxygen in the solutions, PTFE screw caps armed with fluoroelastomer (FETFE) O-rings were used to cap test tubes. All the tubes were placed into a heating block preheated to 120° C. Four reactor tubes were pulled from the heating block at time intervals of 20 minutes. To quench the polymerization, the four tubes were immediately placed in an ice-bath followed by the immediate dilution of the reaction mixture with toluene. A proprietary method was used to determine the concentration of the polystyrene product in the reaction mixture. This method was used to test the antipolymerant activity of the quinone methides QMCinn (Example 1) and QMPh (Example 2), the nitro group-containing antipolymerant DNBP (Example 3), the combination of QMCinn and the ammonium salt TIPA-2-EH (Example 9); the combination of QMPh and the ammonium salt DIHA-2-EH (Example 10); and the combination of QMPh and the ammonium salt TIPA 2-EH (Example 11). Antipolymerant activity of QMCinn, without any ammonium salt, is shown in Table 1.

Example 2: Antipolymerant Activity of QMPh (Comparative)

The antipolymerant activity of 7-phenyl quinone methide (QMPh; 2,6-di-tert-butyl-4-benzylidene-cyclohexa-2,5-dienone; U.S. App. Pub. No. 2006/0163539) was tested at a concentration of 0.679 mmolal along with styrene in accordance with the method described in Example 1. Antipolymerant activity of QMCinn, without any ammonium salt, is shown in Tables 2 and 3.

Example 3: Antipolymerant Activity of DNBP (Comparative)

The antipolymerant activity of the nitro-group containing antipolymerant 2-sec-butyl-4,6-dinitrophenol (DNBP), was tested at a concentration of at 0.679 mmolal in freshly prepared styrene in accordance with the method described in Example 1. Antipolymerant activity of DNBP is shown in Tables 1-3.

Example 4: Synthesis of Triisopropylammonium Acetate Ionic Liquid (TIPA-Ac)

The ammonium salt triisopropylammonium acetate (TIPA-Ac) was prepared using the following process. 30.543 g (151.7 mmoles) of a liquid solution of triisopropanolamine (TIPA; 95% w/w) and 8.73 mL (151.7 mmoles) of concentrated acetic acid (99.6% w/w) were added to 100 g of toluene. The reaction mixture was stirred at ambient temperature until TIPA was dissolved in solution, which turned opaque. After mixing was ceased and upon settling, a bi-liquid formed. The toluene was removed using vacuum to leave a viscous liquid, amber in color.

Example 5: Synthesis of Triisopropylammonium Ethylhexanoate Ionic Liquid (TIPA-EH)

The ammonium salt triisopropylammonium ethylhexanoate (TIPA-EH) was prepared using the following process. 19.411 g (96.41 mmoles) of a liquid solution of triisopropanolamine (TIPA; 95% w/w) and 15.4 mL (14.04 g; 96.41 mmoles) of 2-ethylhexanoic acid were added to 300 g of toluene at ambient temperature.

Example 6: Triethylammonium Acetate (TEA-Ac) Ionic Liquid

The ammonium salt triethylammonium acetate (TEA-Ac) was prepared using the following process. 7.836 g (77.44 mmoles) of a liquid solution of triethylamine (TEA) and 77.44 mmoles acetic acid were added to 300 g of toluene at ambient temperature

Example 7: Synthesis of N,N-Diethylhydroxylammonium 2-Ethylhexanoate Ionic Liquid (DEHA-2-EH)

The ammonium salt N,N-diethylhydroxylammonium 2-ethylhexanoate (DEHA-2-EH) was prepared using the following process. 29.090 g (319.8 mmoles) of a liquid solution of diethylhydroxylamine (DEHA) and 46.586 g (319.8 mmoles) of 2-ethylhexanoic acid were added to 300 g of toluene. The reactants were mixed in the toluene for 10 minutes and then the toluene was removed to yield a yellow and clear liquid.

Example 8: Synthesis of Di(hydroxypropyl)hydroxylammonium 2-Ethylhexanoate Ionic Liquid (DHPHA-2-EH)

The ammonium salt di(hydroxypropyl)hydroxylammonium 2-ethylhexanoate ionic liquid (DHPHA-2-EH) was prepared using the following process. 3.418 g (25.149 mmoles) of a liquid solution of di(hydroxypropyl)-hydroxylamine (DEHA) and 3.627 g (25.149 mmoles) of 2-ethylhexanoic acid were added to 300 g of toluene at ambient temperature

Example 9: Composition of QMCinn and Triisopropanolammonium 2-Ethylhexanoate Ionic Liquid The antipolymerant activity of the combination of QMCinn (see Example 1), used at 0.611 mmolal (concentration reduced by 90% from 0.679 mmolal), and 0.0679 mmolal of TIPA-2-EH (Example 5; used at 11% of the mmolal concentration of QMCinn), was determined in the presence of stabilizer-free styrene using the method described in Example 1. Data for the antipolymerant activity of the combination, as well as QMCinn and DNBP used alone, are shown in Table 1.

The combination of QMCinn and TIPA-2-EH showed improved antipolymerant activity over QMCinn alone over most time points tested, and the improvement became more pronounced over time, with the QMCinn and TIPA-2-EH combination showing greater than a six-fold improvement over QMCinn at the last time point (120 mins), even with QMCinn being used at a lower concentration. QMCinn and TIPA-2-EH combination also performed better than the nitro-group containing antipolymerant DNBP at most time points measured.

TABLE 1

| Time | 0.679 mmolal QMCinn | 0.611 mmolal QMCinn + 0.0679 mmolal Triisopropanolammonium 2-Ethylhexanoate | 0.679 mmolal DNBP |
|---|---|---|---|
| 20  | 0.0379 | 0.0483 | 0.0290 |
| 40  | 0.119  | 0.0669 | 0.0599 |
| 60  | 0.499  | 0.113  | 0.144  |
| 80  | 1.14   | 0.246  | 0.396  |
| 100 | 1.81   | 0.431  | 0.567  |
| 120 | 4.50   | 0.747  | 0.832  |

Example 10: Composition of QMPh and N,N-Diethylhydroxylammonium 2-Ethylhexanoate Ionic Liquid The antipolymerant activity of the combination of 0.611 mmolal of QMPh, and 0.0679 of N,N-diethylhydroxylammonium 2-ethylhexanoate ionic liquid (DIHA-2-EH) was determined in the presence of stabilizer-free styrene using the method described in Example 1. Data for the antipolymerant activity of the combination, as well as QMPh and DNBP used alone, are shown in Table 2.

The combination of QMPh and DIHA-2-EH showed improved antipolymerant activity over QMPh alone at all time points tested, and showed greater than a ten-fold improvement over QMPh at an early time point (20 mins), even with QMPh being used at a lower concentration in the combination. QMPh and DIHA-2-EH combination also displayed antipolymerant activity that was comparable to the nitro-group containing antipolymerant DNBP.

TABLE 2

| Time | 0.679 mmolal QMPh | 0.611 mmolal QMPh + 0.0679 mmolal diethylhydroxylammonium 2-ethylhexanoate | 0.679 mmolal DNBP |
|---|---|---|---|
| 20  | 0.226 | 0.0209 | 0.0290 |
| 40  | 0.436 | 0.0711 | 0.0599 |
| 60  | 0.792 | 0.175  | 0.144  |
| 80  | 0.949 | 0.376  | 0.396  |
| 100 | 1.48  | 0.654  | 0.567  |
| 120 | 2.03  | 0.734  | 0.832  |

Example 11: Composition of QMPh and Triisopropanolammonium 2-Ethylhexanoate Ionic Liquid The antipolymerant activity of the combination of 0.611 mmolal of QMPh and 0.0679 of N,N-triisopropanolammonium 2-ethylhexanoate (TIPA 2-EH) ionic liquid was determined in the presence of stabilizer-free styrene using the method described in Example 1. Data for the antipolymerant activity of the combination, as well as QMPh and DNBP used alone, are shown in Table 3.

The combination of QMPh and TIPA 2-EH showed improved about antipolymerant activity over QMPh alone at all times points tested, ranging from about 1.3-fold to about 4-fold greater antipolymerant activity over QMPh alone, even with QMPh being used at a lower concentration in the combination. QMPh and TIPA 2-EH combination also displayed antipolymerant activity that was comparable to the nitro-group containing antipolymerant DNBP at earlier time points.

TABLE 3

| Time | 0.611 mmolal QMPh + 0.0679 mmolal triisopropanolammonium 2-ethylhexanoate | 0.679 mmolal QMPh | 0.679 mmolal DNBP |
|---|---|---|---|
| 20  | 0.146 | 0.226 | 0.0290 |
| 40  | 0.163 | 0.436 | 0.0599 |
| 60  | 0.197 | 0.792 | 0.144  |
| 80  | 0.372 | 0.949 | 0.396  |
| 100 | 1.02  | 1.48  | 0.567  |
| 120 | 1.53  | 2.03  | 0.832  |

What is claimed is:

1. A composition comprising:
a quinone methide and an ammonium salt, wherein (A) the ammonium salt is present in a molar amount that is less than a molar amount of the quinone methide, (B) the ammonium salt comprises a protonated cation, or both (A) and (B), and wherein the ammonium salt improves an ability of the composition to inhibit polymerization of a polymerizable monomer by more than 1.2-fold as compared to a composition containing the quinone methide but without the ammonium salt under the same conditions.

2. The composition of claim 1 wherein the quinone methide is of Formula I:

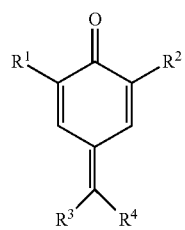

wherein $R^1$ and $R^2$ are independently selected from C4-C18 alkyl, C5-C12 cycloalkyl, phenyl, and C7-C15 cycloalkyl, wherein $R^3$ and $R^4$ are independently selected from —H, C1-C18 alkyl, phenyl, substituted phenyl, C5-C12 cycloalkyl, —CN, —COOH, —C=CHR$^5$, —C≡CR$^5$, —COOR$^5$, —COR$^5$, —OCOR$^5$, —CONHR$^5$, wherein $R^5$ is selected from H, C1-C18 alkyl, C5-C12 cycloalkyl, phenyl, and C7-C15 cycloalkyl, and substituted phenyl.

3. The composition of claim 2 wherein the quinone methide is 2,6-di-tert-butyl-4-benzylidene-cyclohexa-2,5-dienone.

4. The composition of claim 1 wherein the ammonium salt comprises:
(i) a cation of Formula III:

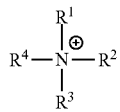

where $R^1$, $R^2$, $R^3$, and $R^4$ are independently selected from (a) —H, (b) a carbon-containing group, (c) an oxygen-containing group, and (d) an oxygen- and carbon-containing group; or
(ii) a cation of Formula IV:

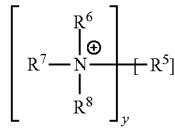

where $R^5$ is a monovalent or multivalent carbon-containing group, y is an integer in the range of 1-4, and $R^6$, $R^7$, and $R^8$ are independently selected from (a)-(d).

5. The composition of claim 4 where in the cation of Formula III: at least three of $R^1$, $R^2$, $R^3$, and $R^4$ are any one or a combination of (b)-(d), or in the cation of Formula IV at least two of $R^6$, $R^7$, and $R^8$ are any one or a combination of (b)-(d).

6. The composition of claim 4 wherein (b) the carbon-containing group consists of carbon, oxygen, and hydrogen, (c) the oxygen-containing group consists of oxygen and hydrogen, (d) the oxygen- and carbon-containing group consists of carbon, oxygen, and hydrogen, or more than one of (b)-(d).

7. The composition of claim 1 wherein the cation of the ammonium salt has (a) a total amount of carbon atoms in the range of 0-18, 1-12, or 2-10; (b) a total amount of oxygen atoms in the range of 0-6, 1-4, or 1-3; (c) a total amount of hydrogen atoms in the range of 4-40, 6-30, or 8-24; or any combination of (a)-(c).

8. The composition of claim 4 wherein the carbon-containing group is selected from C1-C18 alkyl, aryl, alkyl aryl, and aryl alkyl.

9. The composition of claim 4 wherein the carbon-containing group is
(b1) a linear or branched C1-C12 alkyl group, or is selected from the group consisting of methyl, ethyl, propyl, isopropyl, n-butyl, isobutyl, sec-butyl, and tert-butyl, pentyl, hexyl, heptyl, octyl, nonyl, decyl, and dodecyl;

(b2) a C1-C12 cycloalkyl group, or is selected from the group consisting of cyclobutyl, cyclopentyl, cyclohexyl, and cyclooctyl,
(b3) a C1-C14 aryl group, or is selected from the group consisting of phenyl, ethylphenyl, tolyl, naphthyl, and anthracyl; or
(b4) a linear or branched C1-C12 alkylene group, or is selected from the group consisting of allyl and isobutenyl.

10. The composition of claim 4 wherein the oxygen- and carbon-containing group is of Formula VIII:

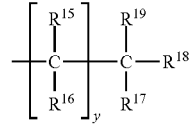

where $R^{15}$, $R^{16}$, $R^{17}$, $R^{18}$, and $R^{19}$ are independently selected from H, $C_1$-$C_{18}$ alkyl, aryl, alkyl aryl, aryl alkyl, and —OR$^{20}$, wherein $R^{20}$ is selected from H, $C_1$-$C_{18}$ alkyl, aryl, alkyl aryl, aryl alkyl, or $R^{16}$ and $R^{17}$ are divalent hydrocarbon-containing groups bonded to one another to form a cyclic alkyl or aryl group, and wherein y is an integer in the range of 1-3, wherein Formula VIII includes at least one —OR$^{20}$ group.

11. The composition of claim 4 wherein the oxygen- and carbon-containing group is a linear or branched C1-C18 hydroxyalkyl group, or is selected from the group consisting of hydroxymethyl, 1- or 2-hydroxyethyl, 1-, 2-, or 3-hydroxypropyl, 2-hydroxyisopropyl, 1-, 2-, 3-, or 4-hydroxybutyl, and 1-, 2-, or 3-hydroxyisobutyl.

12. The composition of claim 4 wherein the oxygen- and carbon-containing group is selected from the group consisting of 2-benzoxazolyl, adipyl, glutaryl, succinyl, malonyl, acetyl, acrylyl, methacrylyl, caproyl, benzoyl, phthaloyl, terephthaloyl, carbethoxy, carbonyl, and formyl.

13. The composition of claim 4 wherein (c1) the oxygen-containing group is hydroxyl, (a1) one of $R^1$, $R^2$, $R^3$, and $R^4$ is —H or one of $R^6$, $R^7$, and $R^8$ is —H, or both (c1) and (a1).

14. The composition of claim 4 wherein the ammonium salt comprises a cation of the Formula VI:

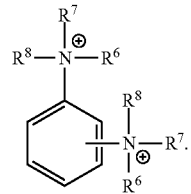

15. The composition of claim 1 wherein the ammonium salt comprises an anion comprising a carboxylate group, a sulfonate group, a phosphonate group, a nitrate group, or a combination thereof.

16. The composition of claim 15, wherein the anion has (a) an amount of carbon atoms in the range of 2-18, 3-12, or 4-10, (b) an amount of oxygen atoms in the range of 2-4, or both (a) and (b).

17. The composition of claim 16, wherein the anion is selected from the group consisting of
acetate (ethanoate);
propionate (propanoate);
butyrate (butanoate), isobutyrate (2-methylpropanoate);

valerate (pentanoate), isovalerate (3-methylbutanoate), 2-methylbutanoate, pivalate (2,2-dimethylpropanoate);

caproate (hexanoate), 2-methylvalerate, 3-methylvalerate, 4-methylvalerate, 2,2-2,2-dimethylbutanoate, 2-ethylbutanoate;

heptanoate (enanthoate), 2-methylcaproate, 3-methylcaproate, 4-methylcaproate, 5-methylcaproate, 2,2-dimethylvalerate, 2-ethylvalerate;

caprylate (octanoate), 2-methylheptanoate, 3-methylheptanoate, 4-methyl heptanoate, 5-methylheptanoate, 6-methylheptanoate, 2,2-dimethylcaproate, 2-ethylcaproate (2-ethylhexanoate), and 2-propylvalerate.

18. The composition of claim 1 wherein the quinone methide is present in a molar amount greater than the ammonium salt.

19. The composition of claim 1 wherein the ammonium salt is in the form of an ionic liquid at room temperature (25° C.).

20. The composition of claim 1 wherein the molar amount of the quinone methide is greater than 1.5-times, greater than 2.5-times, or greater than 5-times the molar amount of the ammonium salt in the composition.

21. The composition of claim 1 having no or less than 50 ppm of a nitroxyl group containing antipolymerant.

22. A composition formed by adding the composition of claim 1 to a hydrocarbon-containing composition comprising a polymerizable monomer, the hydrocarbon-containing composition optionally being a petroleum product.

23. A composition comprising:
a quinone methide and an ammonium salt,
wherein the ammonium salt comprises a cation of Formula VI:

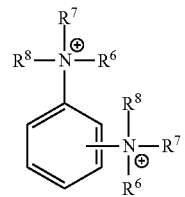

where $R^6$, $R^7$, and $R^8$ are independently selected from (a) —H, (b) a carbon-containing group, (c) an oxygen-containing group, and (d) an oxygen- and carbon-containing group.

24. A method for inhibiting the polymerization of monomers in a composition, the method comprising
providing a composition comprising a polymerizable monomer or a compound capable of forming a polymerizable monomer, a quinone methide, and an ammonium salt,
wherein polymerization of the polymerizable monomer is inhibited in the presence of the quinone methide and the ammonium salt, wherein the ammonium salt improves inhibition of polymerization of the monomer by more than 1.2-fold, as compared to a composition containing the quinone methide but without the ammonium salt under the same conditions.

25. The method of claim 24 wherein the polymerizable monomer is selected from the group consisting of acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyltoluene, and vinylpyridine.

* * * * *